US011029317B2

(12) United States Patent
Sarwal et al.

(10) Patent No.: US 11,029,317 B2
(45) Date of Patent: Jun. 8, 2021

(54) COMPOSITIONS AND METHODS FOR DETECTING ANTI-ENDOTHELIAL CELL ANTIBODIES IN ALLOGRAFT REJECTION

(71) Applicants: IMMUCOR GTI DIAGNOSTICS, INC., Norcross, GA (US); THE JOHNS HOPKINS UNIVERSITY, Baltimore, MD (US)

(72) Inventors: Minnie M. Sarwal, Mountain View, CA (US); Tara Sigdel, Mountain View, CA (US); Annette M. Jackson, Baltimore, MD (US)

(73) Assignees: The Johns Hopkins University, Baltimore, MD (US); Immucor GTI Diagnostics, Inc., Waukesha, WI (US)

( * ) Notice: Subject to any disclaimer, the term of this patent is extended or adjusted under 35 U.S.C. 154(b) by 62 days.

(21) Appl. No.: 15/512,223

(22) PCT Filed: Sep. 18, 2015

(86) PCT No.: PCT/US2015/050924
§ 371 (c)(1),
(2) Date: Mar. 17, 2017

(87) PCT Pub. No.: WO2016/044714
PCT Pub. Date: Mar. 24, 2016

(65) Prior Publication Data

US 2017/0276687 A1 Sep. 28, 2017

Related U.S. Application Data

(60) Provisional application No. 62/058,046, filed on Sep. 30, 2014, provisional application No. 62/052,251, filed on Sep. 18, 2014.

(51) Int. Cl.
*G01N 33/68* (2006.01)
*G01N 33/50* (2006.01)
*G01N 33/564* (2006.01)

(52) U.S. Cl.
CPC ......... *G01N 33/6854* (2013.01); *G01N 33/50* (2013.01); *G01N 33/564* (2013.01); *G01N 33/6893* (2013.01); *G01N 2800/245* (2013.01)

(58) Field of Classification Search
None
See application file for complete search history.

(56) References Cited

U.S. PATENT DOCUMENTS

2006/0211035 A1 9/2006 Itescu
2009/0054358 A1* 2/2009 Small .................. A61K 31/553 514/43

(Continued)

FOREIGN PATENT DOCUMENTS

EP 1884776 A1 2/2008
WO WO-2012122374 A2 * 9/2012 ......... G01N 33/6893
WO WO-2013/142796 A2 9/2013

OTHER PUBLICATIONS

Written Opinion and International Search Report issued in International Application No. PCT/US2015/050924 dated Jan. 29, 2016.

(Continued)

*Primary Examiner* — David W Berke-Schlessel
(74) *Attorney, Agent, or Firm* — Mintz, Levin, Cohn, Ferris, Glovsky and Popeo, P.C.

(57) ABSTRACT

Provided herein are methods, compositions, and kits for diagnosing allograft rejection of organ transplants by identifying the presence of anti-endothelial cell antibodies. Such methods and compositions are independent of external con- (Continued)

founders such as recipient age, transplant center, assay, cause of end-stage disease, co-morbidities, immunosuppression usage, and the like.

29 Claims, 7 Drawing Sheets

(56) References Cited

U.S. PATENT DOCUMENTS

| | | | |
|---|---|---|---|
| 2013/0004978 | A1 | 1/2013 | Hebert et al. |
| 2013/0252839 | A1 | 9/2013 | Elhanan et al. |

OTHER PUBLICATIONS

Li, W et al., "CTLA4 Engagement is Required for Induction of Murine Liver Transplant Spontaneous Tolerance." American Journal of Transplantation. 2005; vol. 5, pp. 978-986; abstract.

Kwalczyk, A., et al., "Cell-Extrinsic CTLA4-Mediated Regulation of Dendritic Cell Maturation Depends on STAT3." European Journal of Immunology. Apr. 2014, vol. 44, pp. 1143-1155, DOI: 10.1002/eji.2013436011; abstract, p. 1153, first column, third paragraph, p. 1153, second column, fourth paragraph.

D'Brien, "Autoimmune haemolytic anaemia comlpicating haematopoietic cell transplantation in paediatric patients: high incidence and significance mortality in unrelated donor transplants for non-malignant diseases." 2004 Blackwell Publishing Ltd, British Journal of Haematology, No. 127, pp. 67-75 ; doi: 10.111/j. 1365-2141.2004.05138.x.

Dragun et al. (Feb. 10, 2005) "Angiotensin II Type 1-Receptor Activating Antibodies in Renal-Allograft Rejection," New England Journal of Medicine. 352(6):558-569.

Grandtnerova et al. (Sep. 2008) "Hyperacute Rejection of Living Related Kidney Grafts Caused by Endothelial Cell-Specific Antibodies: Case Reports," Transplantation Proceedings, 40(7):2422-2424.

Matsui et al. (Apr. 1, 1999) "Autoantibodies to T Cell Costimulatory Molecules in Systemic Autoimmune Diseases," The Journal of Immunology. 162(7):4328-4335.

Tait et al. (Mar. 2009) "Review article: Luminex technology for HLA antibody detection in organ transplantation," Nephrology. 14(2);247-254.

* cited by examiner

B.

A.

COMPOSITIONS AND METHODS FOR DETECTING ANTI-ENDOTHELIAL CELL ANTIBODIES IN ALLOGRAFT REJECTION

CROSS-REFERENCE TO RELATED APPLICATIONS

This application is a 371 national stage entry of International Patent Application No. PCT/US2015/050924 filed Sep. 18, 2015, which claims priority to U.S. Provisional Application No. 60/052,251, filed Sep. 18, 2014, and U.S. Provisional Application No. 62/058,046, filed Sep. 30, 2014, the disclosure of each of which is incorporated herein by reference in its entirety.

FIELD OF THE INVENTION

The disclosure relates to methods, compositions, and kits for the assessment of allograft rejection by the specific detection of anti-endothelial cell antibodies.

BACKGROUND OF THE INVENTION

Organ transplantation from a donor to a host recipient is a component of certain medical procedures and treatment regimes. Following transplantation, it is necessary to avoid graft rejection by the recipient. In order to maintain viability of the donor organ, immunosuppressive therapy is typically employed. Nevertheless, organ transplant rejection can still occur. Organ transplant rejection is classified as hyperacute, acute, borderline acute, subclinical acute, or chronic. For most organs, including kidneys, organ rejection can be unequivocally diagnosed only by performing a biopsy of that organ after it has been transplanted. Detecting injury in a timely fashion is crucial to ensuring allograft health and long-term survival. Particularly important is being able to assess whether an organ transplant will be survive in a donor recipient before transplantation occurs. This pre-transplant assessment would allow for a better matching of organ donors and organ recipients, and would increase the survivability of limited numbers of organs available for transplantation.

Improvements in the ability to detect alloantibodies in the sera of transplant recipients both prior to and following renal transplantation, along with the development of methods to identify antibody mediated damage have highlighted the role of antibodies in both acute and chronic allograft rejection (McKenna, R. M. et al. *Transplantation* 2000, 69, 319-326; Mengel, M. et al. *Am J Transplant* 2012, 12, 563-570; Sis, B. et al. *Am J Transplant* 2012, 12, 1168-1179; Loupy, A. et al. *Nat Rev Nephrol* 2012 8, 348-357). However, the majority of these studies have focused on HLA-specific antibodies and their potential to activate complement. The clinical relevance and mechanisms for how alloantibodies can contribute to allograft rejection in the absence of complement activation, such as in the case of low level HLA antibodies, are currently under investigation (Morrell, C. N. et al. *Circ Res* 2008, 102, 777-785; Zhang, X. et al. *Curr Opin Organ Transplant* 2012 17, 446-451). Reports of allograft rejection in HLA identical sibling transplants suggest a role for non-HLA antibodies in some rejections (Opelz, G. *Lancet* 2005, 365, 1570-1576; Grafft, C. A. et al. *Nephrol Dial Transplant* 2010 25, 307-310). Non-HLA antigens that have been associated with renal allograft rejection include: agrin, vimentin, perlecan, Kα-tubulin, protein kinase C zeta, the major histocompatibility complex class I-related chain A (MICA), and angiotensin II type 1 receptor (AT1R) (Sigdel, T. K. and Sarwal M. M. *Hum Immunol* 2013 74, 1486-1490).

Non-HLA antigens expressed on endothelial cells are of particular interest given that the vascular endothelium serves as the point of con12 11tact between the recipient's immune system and the transplanted allograft. Therefore, anti-endothelial cell antibodies (AECAs) reactive to these 12 non-HLA antigens may have an important pathogenic role in allograft rejection. HLA incompatible transplantation has revealed that patients transplanted across both HLA and AECA barriers have an increased incidence and severity of antibody mediated rejection.

This has led to a need for new methods of detection of non-HLA mediated AECA humoral responses that will contribute to an allograft rejection response post-transplantation. New specific endothelial cell crossmatching tests for organ donors and organ recipients prior to transplantation will provide for a needed method to identify patients that would not otherwise be identified as high-risk for incurring an allograft rejection. Studies using peripheral blood, endothelial cell precursors (ECPs) as targets indicated that non-sensitized recipients transplanted across a react positive endothelial cell crossmatch experienced increased rejection and higher serum creatinine values early post-transplantation, indicating an early acute rejection response (Breimer, M. E. et al. *Am J Transplant* 2008). These prior methods of endothelial cell cross-matching further described by Sumatran et al., U.S. Pat. No. 8,034,635, utilize ECPs from donors to be reacted with recipient serum for the detection of AECAs that may be responsible for complement independent allograft rejection. Although this endothelial cell crossmatch test has been shown to be clinically useful, it has many technical problems. Accordingly, this testing strategy relies on the detection of recipient IgG and IgM antibodies as a general read out of AECAs. This approach is limited because HLAs are expressed on ECPs from donors, which limits the ability for specifically detecting AECAs in HLA incompatible recipients. Thus, without knowing specific and conserved AECA antigens, the indentification of patients proceeding to transplant across both barriers is impeded. Therefore, identification of new and specific antigenic targets expressed on ECPs would provide for a currently unavailable diagnostic test for AECAs in solid-phase immunoassays that, in turn, may help in pre-transplant risk assessment and provide an opportunity for therapeutic intervention.

Thus, described herein, are novel AECA antigenic targets and methods, compositions, and kits for the sensitive and accurate identification of AECAs that correlate with increased in vivo microvascular injury in patients testing positive for these AECAs.

All patents, patent applications, publications, documents, and articles cited herein are incorporated herein by reference in their entireties, unless otherwise stated.

BRIEF SUMMARY OF THE INVENTION

Disclosed herein are compositions and methods for classifying an individual as being at high risk for an allograft rejection (AR) and/or for being at low risk or no risk for an allograft rejection (no-AR) of organ transplants. These compositions and methods can be used in such classification in both pediatric and adult patients, comprising the level of a set of anti-endothelial cell antibodies.

In one embodiment described herein, is a method of diagnosing an AR in an individual who has received or will receive an organ transplant, the method comprising the steps of: a) isolating at least one antibody from a biological sample from an individual that forms an affinity interaction with at least a portion or peptide fragment of at least one protein selected from Table 2, b) measuring a level of the at least one antibody, c) comparing the level of the at least one antibody from an individual to a positive reference standard and comparing the level of the at least one antibody to a negative reference; and wherein a similarity of the measured level of the at least one antibody to the positive reference standard indicates increased risk of developing AR and a similarity of the measured level of the at least one antibody to the negative reference standard indicates reduced risk of developing AR.

In one embodiment described herein is a method of treating an individual who has recieved an organ transplant the method comprising ordering a clinical test comprising the steps of: a) isolating at least one antibody from a biological sample from an individual that forms an affinity interaction with at least a portion or peptide fragment of at least one protein selected from Table 2, b) measuring a level of the at least one antibody, c) comparing the level of the at least one antibody from an individual to a positive reference standard and comparing the level of the at least one antibody to a negative reference; and wherein a similarity of the measured level of the at least one antibody to the positive reference standard indicates increased risk of developing AR and a similarity of the measured level of the at least one antibody to the negative reference standard indicates reduced risk of developing AR; and wherein an administration of a therapeutically effective amount of one or more of a therapeutic agents is increased in a subject indicated as having an AR, an administration of a therapeutically effective standard of care amount of one or more of a therapeutic agent is maintained in a subject indicated as not having an AR, or an administration of a therapeutically effective amount of one or more of a therapeutic agent is decreased in a subject indicated as not having an AR.

In some of the embodiments described herein, the method comprises a solid-phase immunoassay. In some of the embodiments described herein, the solid-phase immunoassay comprises an ELISA. In some of the embodiments described herein, the individual is an adult aged 23 years or older. In some of the embodiments described herein, the individual is a child or young adult under the age of 23. In some of the embodiments described herein, the sample comprises a recipient serum sample. In some of the embodiments described herein, the at least one antibody comprises an anti-endothelial cell antibody. In some of the embodiments described herein, the anti-endothelial cell antibody can form an affinity interaction with at least one protein selected from the group consisting of endoglin, Fms-like tyrosine kinase-3 (FLT3) ligand, EGF-like repeats and discoidin I-like domains 3 (EDIL3) and intercellular adhesion molecule 4 (ICAM4). In some of the embodiments described herein, the isolating of at least one antibody comprises incubating a sample having the antibody with an antibody capture element. In some of the embodiments described herein, the antibody capture element comprises an antibody specific antigen, a capture bead, or capture solid support. In some of the embodiments described herein, the antibody capture element comprises an antibody specific antigen. In some of the embodiments described herein, the antibody specific antigen is selected from the group consisting of: a full length protein, protein fragment, peptide, polypeptide, recombinant peptide, recombinant protein, and a polypeptide fragment. In some of the embodiments described herein, the full length protein, protein fragment, peptide, polypeptide, recombinant peptide, recombinant protein, and a polypeptide fragment comprises at least a portion or peptide fragment of at least one or more of the proteins in Table 2. In some of the embodiments described herein, the full length protein, protein fragment, peptide, polypeptide, recombinant peptide, recombinant protein, and a polypeptide fragment comprises at least a portion or peptide fragment of one or more proteins selected from the group consisting of endoglin, Fms-like tyrosine kinase-3 (FLT3) ligand, EGF-like repeats and discoidin I-like domains 3 (EDIL3) and intercellular adhesion molecule 4 (ICAM4). In some of the embodiments described herein, the antibody specific antigen is labelled with an isolation tag selected from the group consisting of biotin, a GST tag, an amide group, and a streptavidin tag. In some of the embodiments described herein, the isolation tag comprises biotin. In some of the embodiments described herein, the antibody capture element is isolated with a secondary capture element. In some of the embodiments described herein, the secondary capture element is immobilized on a solid support comprising a bead or a plate. In some of the embodiments described herein, the secondary capture element comprises streptavidin. In some of the embodiments described herein, the level of the antibody is measured by a detection element. In some of the embodiments described herein, the detection element comprises a labelled secondary antibody. In some of the embodiments described herein, the level of at least one measured antibody is compared to the positive and negative reference standards by a computer program, wherein after the comparison, the computer program outputs a score indicating the likelihood of an individual having an AR response.

In some of the embodiments described herein, the methods described herein further comprise detecting a donor specific HLA antibody, wherein the presence of the donor specific HLA antibody indicates a risk for developing an AR. In some of the embodiments described herein, detecting a donor specific HLA antibody comprises a cell based assay or a solid-phase immunoassay. In some of the embodiments described herein, the solid-phase immunoassay comprises an ELISA or Luminex assay and the cell based assay comprises a cross-match assay.

In some of the embodiments described herein, the method of diagnosing an AR in an individual prior to receiving a solid organ transplant, further comprises the steps of performing an endothelial cell cross-match test between an organ donor and organ recipient.

In some of the embodiments described herein, the endothelial cell cross-match test comprises the steps of: a) isolating donor endothelial cell progenitor cells (ECP)s from a donor blood sample, b) obtaining recipient serum sample, c) incubating the isolated donor ECPs with the recipient serum sample; and d) isolating at least one antibody from the ECPs that forms an affinity interaction with at least a portion or peptide fragment of at least one protein selected from Table 2. In some of the embodiments described herein, the at least one antibody is an anti-endothelial cell antibody. In some of the embodiments described herein, the anti-endothelial cell antibody forms an affinity interaction with at least one protein selected from the group consisting of endoglin, Fms-like tyrosine kinase-3 (FLT3) ligand, EGF-like repeats and discoidin I-like domains 3 (EDIL3) and intercellular adhesion molecule 4 (ICAM4).

In some of the embodiments described herein, the method of diagnosing an AR in an individual who has received or will receive an organ transplant further comprises a cell based assay. In some of the embodiments described herein, the cell based assay comprises a CDC cross-match test or flow cytometry cross-match assay. In some of the embodiments described herein, the individual may be positive or negative for HLA specific antibodies. In some of the embodiments described herein, the individual may test positive or negative in an endothelial cell cross-match test. In some of the embodiments described herein, the individual may test positive or negative in a CDC cross-match test.

In one embodiment described herein are kits for diagnosing an AR in an individual who has received or will receive an organ transplant, the kit comprising: a) an antibody capture element for isolating at least one antibody from a biological sample from an individual that forms an affinity interaction with at least a portion or peptide fragment of at least one protein selected from Table 2, b) a detection element for measuring a level of the at least one antibody, c) a positive reference standard and a negative reference standard for comparing the level of the at least one antibody from an individual to a positive reference standard and comparing the level of the at least one antibody to a negative reference.

In one aspect, the kit comprises a solid-phase immunoassay. In another aspect, the kit comprises a solid-phase immunoassay comprising an ELISA. In another aspect, the kit comprises an antibody capture element. In another aspect, the kit comprises an antibody capture element comprising an antibody specific antigen, a capture bead, or capture solid support. In another aspect the kit comprises an antibody capture element comprising an antibody specific antigen. In another aspect the kit comprises an antibody specific antigen comprising a full length protein, protein fragment, peptide, polypeptide, recombinant peptide, recombinant protein, and a polypeptide fragment. In another aspect the kit comprises an antibody specific antigen comprising a full length protein, protein fragment, peptide, polypeptide, recombinant peptide, recombinant protein, or a polypeptide fragment comprising at least a portion or peptide fragment of one or more of the proteins in Table 2. In another aspect, the kit comprises a full length protein, protein fragment, peptide, polypeptide, recombinant peptide, recombinant protein, and a polypeptide fragment comprising at least a portion or peptide fragment of one or more proteins selected from the group consisting of endoglin, Fms-like tyrosine kinase-3 (FLT3) ligand, EGF-like repeats and discoidin I-like domains 3 (EDIL3) and intercellular adhesion molecule 4 (ICAM4). In another aspect, the kit comprises an antibody specific antigen described herein labelled with an isolation tag selected from the group consisting of biotin, a GST tag, an amide group, and a streptavidin tag. In another aspect, the kit comprises an antibody specific antigen described herein labelled with an isolation tag isolation tag comprising biotin. In another aspect the kit comprises a secondary capture element. In another aspect, the kit comprises a secondary capture element immobilized on a solid support comprising a bead or a plate. In another aspect the kit comprises a secondary capture element comprising streptavidin. In another aspect, the kit comprises a detection element. In another aspect the kit comprises a detection element comprising a labelled secondary antibody. In another aspect, the kit comprises a computer program wherein the computer program compares the level of at least one measured antibody to the positive and negative reference standards, and wherein after the comparison, the computer program outputs a score indicating the likelihood of an individual having an AR. In another aspect, the kit comprises an element for detecting a donor specific HLA antibody, wherein the presence of the donor specific HLA antibody may indicate an increased risk for developing an AR. In another aspect, the kit comprises the detecting element for detecting a donor specific HLA antibody comprising a cell based assay or a solid-phase immunoassay further comprising an ELISA or Luminex assay.

In another aspect, the kit further comprises a set of reagents for performing an endothelial cell cross-match test between an organ donor and organ recipient. In another aspect, the kit comprises an endothelial cell cross-match test comprising a set of reagents for: a) isolating donor endothelial cell progenitor cells (ECP)s from a donor blood sample, b) obtaining recipient serum sample, c) incubating the isolated donor ECPs with the recipient serum sample; and d) isolating at least one antibody from the endothelial cell progenitor cells. In another aspect, the kit further comprises reagents for performing a cell based assay comprising a CDC cross-match assay or flow cytometry cross-match assay.

Shown are renal biopsies with positive histological scores >1 acquired during the 1.5 years post-transplantation according to protocol or at time of dysfunction. Histological scoring (0-3) was performed using updated Banff '97 criteria 26-29. Shown are grades for glomerulitis (g), interstitial (i) and tubular (t) inflammation, vasculitis (v), peritubular capillaritis (ptc). C4d staining was performed on frozen tissue by indirect immunofluorescence. Transplant glomerulopathy (cg) defined by duplication of the glomerular basement membrane as observed on electron and light microscopy. Low level DR52 HLA-DSA (MFI<1000) was detected in one recipient at time of biopsy.

Figure 2A:
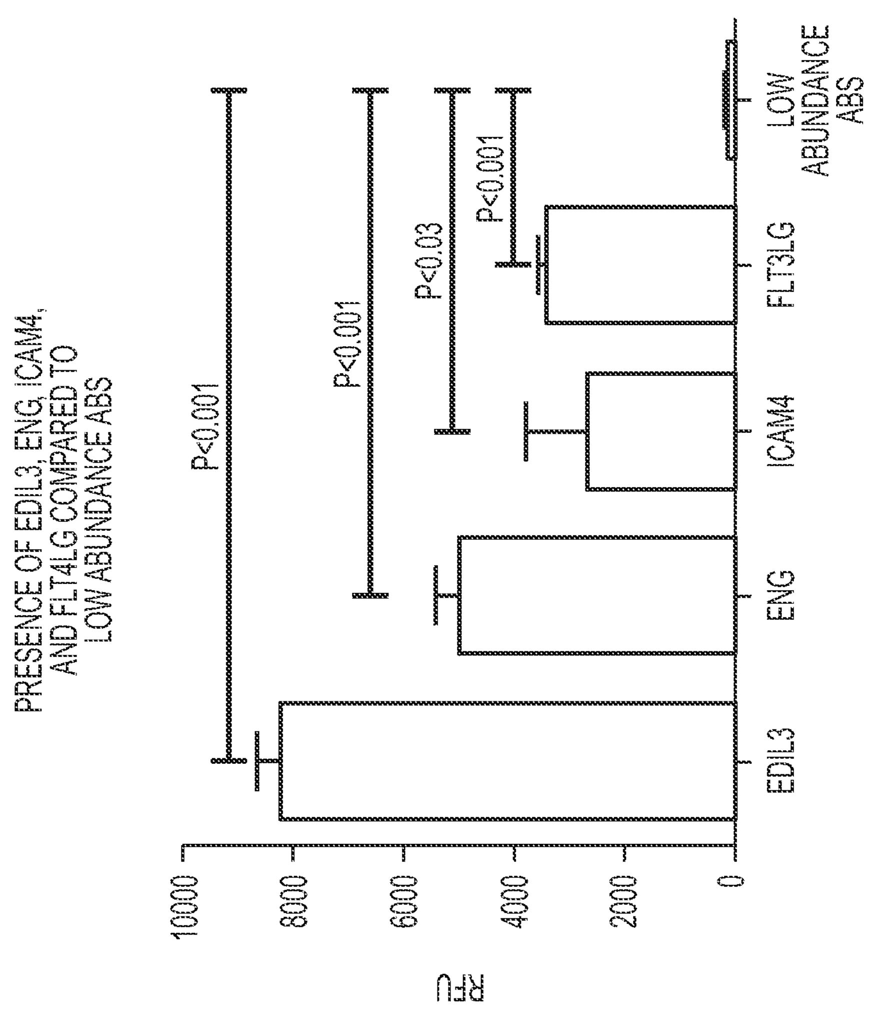
Figure 2B:
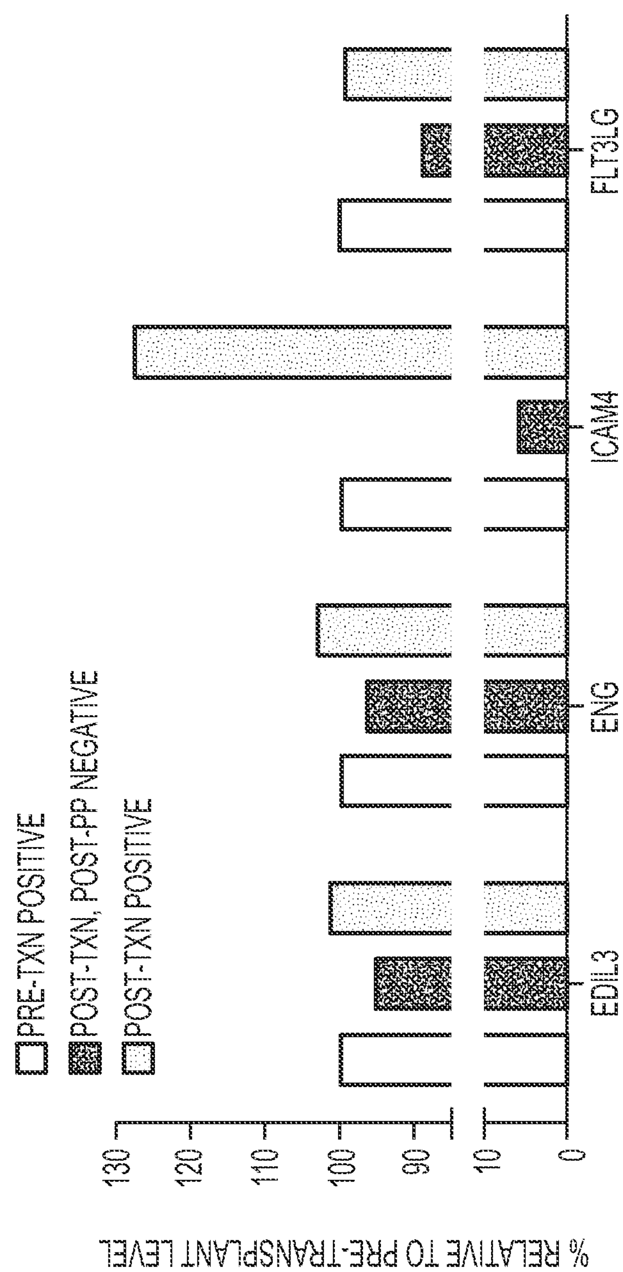

FIG. 2 Identification of Antigenic Targets for AECAs and the Impact of Desensitization Treatment.

Protein array analysis of 14 AECA eluates derived from EC crossmatch positive sera. Relative fluorescence units (RFU) for antibodies specific for EDIL3, endoglin (ENG), ICAM4, and FLT3 Ligand (LG) were significant when compared to the mean signal intensity of low abundance antibodies. We defined a positive threshold of 2000 RFU as a cutoff for abundance. The error bars represent standard error of the mean. B. Impact of plasmapheresis/IVIg (PP) on AECA levels. AECAs specific for endoglin, FLT3 LG, EDIL3 and ICAM4 decreased following PP treatments and rebounded in a post-transplant serum that yielded a positive EC crossmatch test. Data shown are from a single renal recipient, values were normalized to total IgG immunoglobulin.

Figure 3:
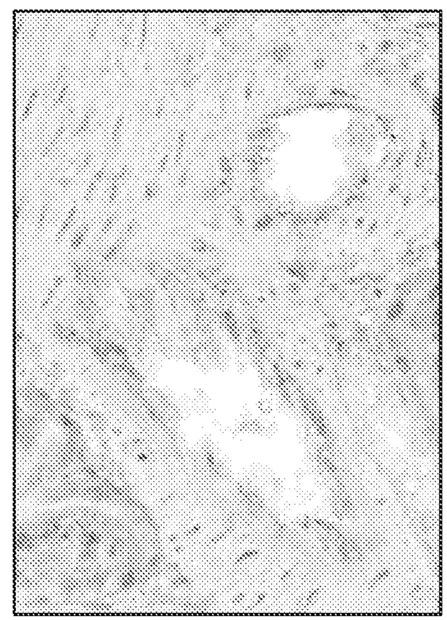
Figure 3:
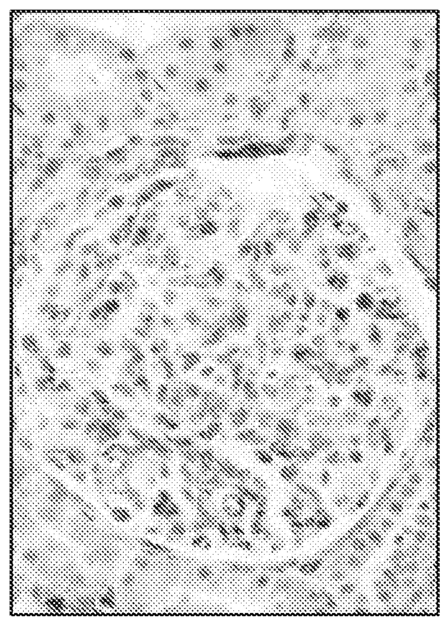
Figure 3:
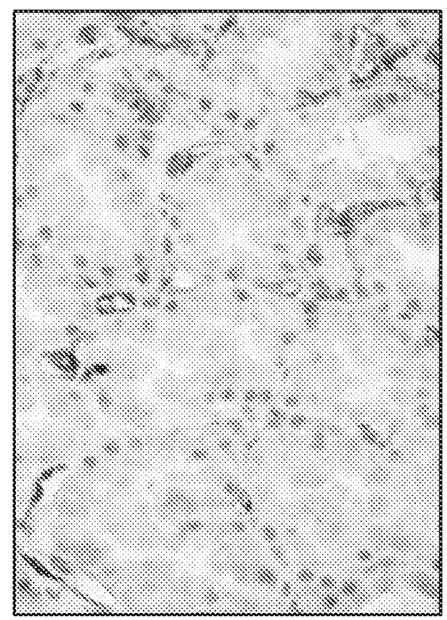

FIG. 3 Expression of Endoglin and FLT3 on Renal Endothelium.

Immunohistochemistry performed on biopsies taken at time of rejection show expression of (A) endoglin and (B) FLT3 on glomerular and peritubular microvasculature and arteries. Data shown is representative of biopsies tested from nine Discovery Cohort recipients.

Figure 4:
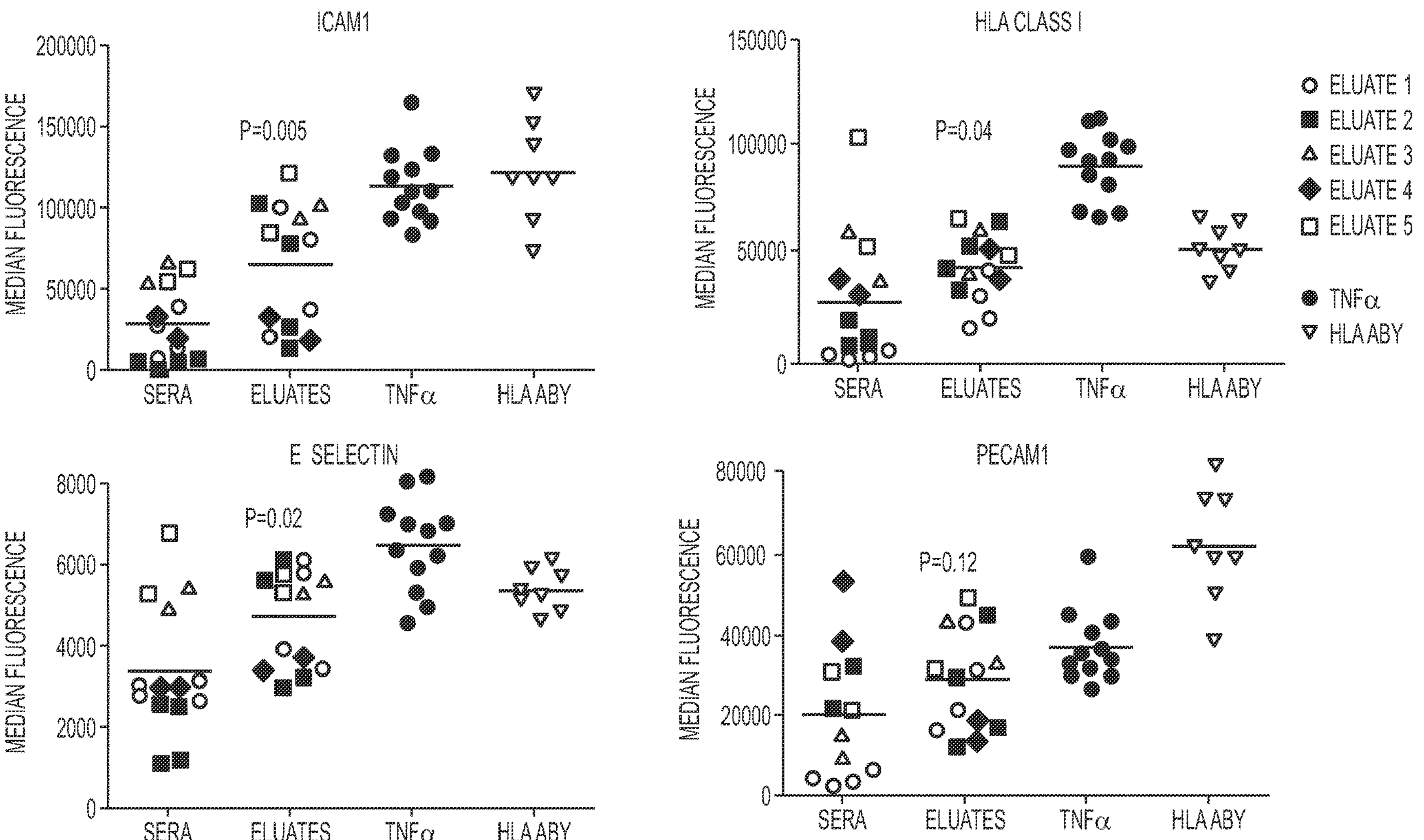

FIG. 4 Endothelial Cell Cultures Stimulated with AECA Eluates Upregulate Markers of Activation.

Primary endothelial cell cultures were stimulated with AECA positive sera, AECA eluates, TNFα (10 ng/well), or an HLA antibody positive serum. Cell surface phenotype analysis was performed 24 hours post stimulation using flow cytometry. Comparisons of median fluorescence values were made between cells stimulated with concentrated AECA eluates and recipient sera (p values shown). Cumulative data obtained from 7 independent experiments, testing AECA eluates from 5 Discovery Cohort recipients FIG. 5. Endothelial Cell Cultures Stimulated with AECA Eluates Differentially Impact Production of Inflammatory Cytokines and Chemokines.

Primary endothelial cell cultures were stimulated with culture media alone, AECA eluates, an HLA antibody positive serum, or TNFα (10 ng/well). Culture supernatant was tested 72 hours post stimulation using a Procarta® human 54 analyte immunoassay acquired on a Luminex® xMAP® multiplex platform. Median fluorescent intensity (MFI) for differentially expressed analytes and positive control standards are shown. Data are representative of 4 independent experiments, testing AECA eluates derived from 5 Discovery Cohort recipients. Production of inflammatory cytokines PDGF, RANTES (also known as CCL5), and RESISTIN were increased following stimulation with the AECA eluates when compared to negative controls (p=3.8×10-13, p=2.1×10-14, p=1.1×10-10 respectively) or cells stimulated with TNFα or HLA antibodies (p=1.8×10-13, p=7.7×10-6, and p=0.002 respectively). In contrast, chemokines CCL3, CCL4, CXCL5, and CXCL appeared decreased in cultures stimulated with the AECA eluates compared to stimulation with TNFα or HLA antibodies (p=6.4×10-5, p=0.05, p=0.07, and p=0.04 respectively).

Figure 6:
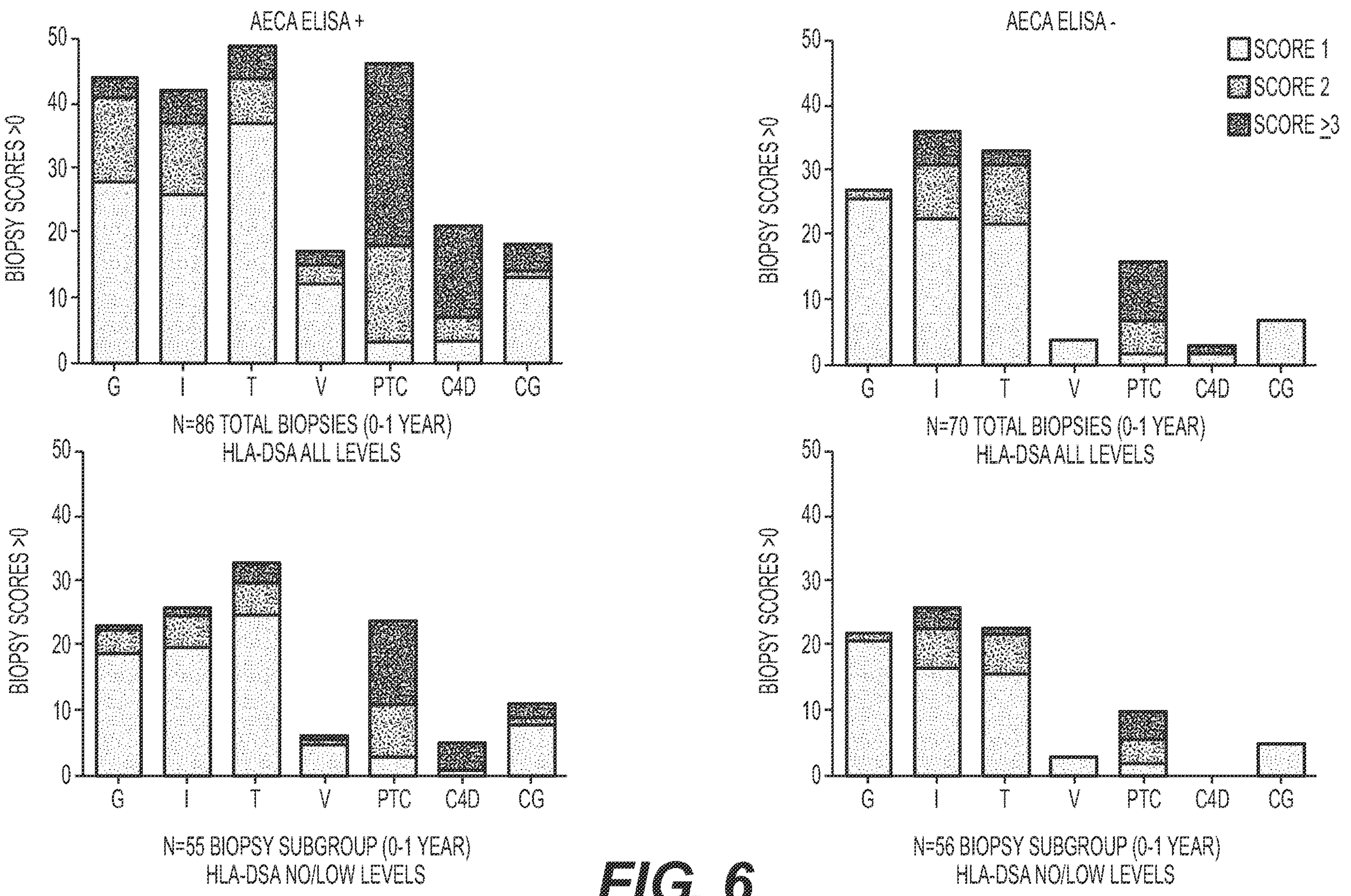

FIG. 6. Histological Scores for AECA ELISA Strongly Positive (n=28) and Negative (n=24) Recipients.

Renal biopsies with positive histological scores >1 acquired during the first year post-transplantation taken according to protocol or at time of dysfunction. Shown are scores from all biopsies or a subset of biopsies when HLA-DSA was not detected at time of biopsy or detected at a negative flow cytometric crossmatch level 20. Histological scoring (0-3) was performed using updated Banff '97 criteria 26-29. Shown are grades for glomerulitis (g), interstitial (i) and tubular (t) inflammation, vasculitis (v), peritubular capillaritis (ptc). C4d staining was performed on frozen tissue by indirect immunofluorescence. Transplant glomerulopathy (cg) defined by duplication of the glomerular basement membrane as observed on electron and light microscopy. Statistics (mean and T-test comparisons) are provided in Table 5.

DETAILED DESCRIPTION OF THE INVENTION

Described herein are a group of anti-endothelial cell antibodies (AECAs), which can aid in determining whether an individual who will receive or has received an organ transplant is undergoing, or will undergo, an allograft rejection (AR) of the transplanted organ. The presence of the AECAs described herein is independent of recipient age, transplant center, sample source, assay, cause of end-stage disease, co-morbidities, immunosuppression usage and the like. Further described herein are methods for assessing AR or no-AR in an individual who will receive or who has received an organ allograft, as well as methods of identifying an individual for treatment of AR in an organ transplant. The invention further provides for kits based on these methods to assess AR and the probability of AR in an individual who will receive or has received an organ allograft.

The methods described herein may be used to monitor a variety of different types of organ allografts. Organ allografts of interest include, but are not limited to: transplanted heart, kidney, lung, liver, pancreas, pancreatic islets, brain tissue, stomach, large intestine, small intestine, cornea, skin, trachea, bone, bone marrow, muscle, bladder or parts thereof. A plurality of biological samples may be collected at any one time. A biological sample or samples may be taken from a subject at any time, including before allograft transplantation, at the time of transplantation, or at any time following transplantation.

Definitions

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

"Allograft rejection" or "AR" is the rejection by the immune system of a tissue/organ transplant recipient when the transplanted tissue is immunologically foreign. "Allograft rejection" or "AR" as used herein further encompasses the terms "acute rejection" or "chronic rejection" AR can be characterized by infiltration of the transplanted tissue by immune cells of the recipient, which carry out their effector function and destroy the transplanted tissue. AR can also be characterized by development of donor-specific antibodies, a diagnosis referred to as antibody-mediated rejection (AMR). AR can be further classified as hyperacute, acute, borderline acute, or subclinical AR. The onset of hyperacute rejection is generally rapid and generally occurs in humans within minutes to hours after transplant surgery. The onset of AR generally occurs in humans within months, often approximately 6-12 months after transplant surgery. Borderline acute and subclinical AR is the result of low grade inflammatory alloresponses. Generally, AR can be treated, inhibited, or suppressed with immunosuppressive drugs such as rapamycin, cyclosporine A, anti-CD40L monoclonal antibodies, and the like.

"No allograft rejection" or "no-AR" or "Stable" or "STA" is used interchangeably herein. No-AR/STA represents a patient at low risk or no risk of AR following transplantation. No-AR can be characterized by the long-term graft survival of transplanted tissue that is immunologically foreign to a tissue transplant recipient.

The term "allograft" refers to a transplant from one individual to another individual, and encompasses any transplanted organ.

As used herein, "gene" refers to a nucleic acid comprising an open reading frame encoding a polypeptide, including exon and (optionally) intron sequences. The term "intron" refers to a DNA sequence present in a given gene that is not translated into protein and is generally found between exons in a DNA molecule. In addition, a gene may optionally include its natural promoter (i.e., the promoter with which the exon and introns of the gene are operably linked in a non-recombinant cell), and associated regulatory sequences, and may or may not include sequences upstream of the AUG start site, untranslated leader sequences, signal sequences, downstream untranslated sequences, transcriptional start and stop sequences, polyadenylation signals, translational start and stop sequences, ribosome binding sites, and the like.

As used herein, the term "isolate" or "isolated" refers to the separation or immobilization of a biological material from a complex biological mixture or sample. In some embodiments described herein, one or more antibodies may be isolated from a complex biological mixture or sample. In some aspects, the one or more antibodies isolated using the methodologies described herein may comprise one or more anti-endothelial cell antibodies.

The term "reference" or "reference standard" refers to a known value or set of known values against which an observed value may be compared. In one embodiment, the reference standard is the value (or level) of anti-endothelial cell antibodies present a graft survival phenotype. In another embodiment, the reference standard is the value (or level) of anti-endothelial cell antibodies present in a graft loss phenotype.

An "individual" or "subject" can be a "patient." A "patient" refers to an "individual" who is under the care of a treating physician. The patient can be male or female. In one embodiment, the patient has received an organ transplant. In another embodiment, the patient has received an organ transplant and is underdoing AR.

A "patient sub-population," and grammatical variations thereof, as used herein, refers to a patient subset characterized as having one or more distinctive measurable and/or identifiable characteristics that distinguishes the patient subset from others in the broader disease category to which it belongs.

The term "sample," as used herein, refers to a composition that is obtained or derived from an individual that contains genomic or proteomic information. In one embodiment, the sample is blood serum. In one aspect, the sample is blood serum from a donor. In another aspect, the sample is blood serum from a recipient. In another embodiment, the sample is whole blood. In another embodiment, the sample is blood. In another embodiment, the sample is peripheral blood leukocytes. In another embodiment, the sample is peripheral blood mononuclear cells. In another embodiment, the sample is a tissue biopsy. In another embodiment, the sample is a tissue biopsy from a transplanted organ. In another embodiment, the sample is a tissue biopsy from an organ prior to transplantation in a recipient.

As used herein, "microarray" refers to an arrangement of a collection of nucleotide sequences in a centralized location. Arrays can be on a solid substrate, such as a surface composed of glass, plastic, or silicon. The nucleotide sequences can be DNA, RNA, or any permutation thereof. The nucleotide sequences can also be partial sequences from a gene, primers, whole gene sequences, non-coding sequences, coding sequences, published sequences, known sequences, or novel sequences.

The term "anti-endothelial cell antibody" or "AECA" as used herein refers to an antibody that has an affinity interaction with an antigen expressed on any type of endothelial cell. In some aspects, the anti-endothelial cell antibody is generated from an allograft recipient that is specific to an endothelial antigen presented on an endothelial cell from a donor allograft.

The term "endothelial cell" as used herein refers to any cell comprising the vasculature of any organ or organ system (e.g., an endothelial cell comprising a capillary, venule, vein, arteriol or artery). In some aspects, the endothelial cell may comprise the vasculature of a transplanted organ or allograft. In some aspects, the endothelial cell comprises the vasculature of a transplanted heart, kidney, lung, liver, pancreas, pancreatic islets, brain tissue, stomach, large intestine, small intestine, cornea, skin, trachea, bone, bone marrow, muscle, or bladder.

The term "endothelial cell progenitor" or "ECP" as used herein refers to a population of cells that circulate in the blood and readily differentiate into an endothelial cell (Asahara, T. et al. *Science* 1997, 275, 964-967). In some aspects, ECPs can be detected by the expression of Tie-2. In some aspects described herein, ECPs are isolated from donor peripheral blood with a binding agent specific for Tie-2. U.S. Pat. Nos. 8,173,372 and 8,034,635 are incorporated by reference for their specific teachings thereof.

The term endothelial cell antigen as used herein refers to any antigen (e.g., any protein, polysaccharide, or glycoprotein) expressed on an endothelial cell. In some aspects described herein are specific endothelial cell antigens that are an immunogen for an antibody (e.g., an antibody specific antigen). In some aspects described herein are specific endothelial cell antigens that are an immunogen for an anti-endothelial cell antibody (e.g., an anti-endothelial cell antibody specific antigen).

"Predicting," "prediction," and "likelihood" as used herein does not mean that the outcome is occurring with 100% certainty. Instead, it is intended to mean that the outcome is more likely occurring than not. Acts taken to "predict," "make a prediction," or "predict the likelihood of" can include the determination of the likelihood that an outcome is more likely occurring than not. Assessment of multiple factors described herein can be used to make such a determination or prediction.

By "compare" or "comparing" is meant correlating, in any way, the results of a first analysis with the results of a second and/or third analysis. For example, one may use the results of a first analysis to classify the result as more similar to a second result than to a third result. With respect to the embodiment of AR assessment of biological samples from an individual, one may use the results to determine whether the individual is undergoing an AR response. With respect to the embodiment of no-AR assessment of biological samples from an individual, one may use the results to determine whether the individual is undergoing a no-AR response.

The terms "assessing" and "determining" are used interchangeably to refer to any form of measurement, and include both quantitative and qualitative measurements. For example, "assessing" may be relative or absolute.

The term "diagnosis" is used herein to refer to the identification or classification of a molecular or pathological state, disease, or condition. For example, "diagnosis" may refer to identification of an organ rejection. "Diagnosis" may also refer to the classification of a particular sub-type of organ rejection, such as AR.

As used herein, "treatment" refers to clinical intervention in an attempt to alter the natural course of the individual being treated. Desirable effects of treatment include reducing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving improved prognosis. In certain embodiments, treatment refers to decreasing the rate of disease progression, ameliorating or palliating the disease state, and achieving improved prognosis of AR in an individual. In some embodiments, treatment refers to a clinical intervention that modifies or changes the administration a treatment regimen of one or more of a therapeutic agent in a subject.

Reference to "about" a value or parameter herein includes (and describes) embodiments that are directed to that value or parameter per se. For example, description referring to "about X" includes description of "X". The term "about" is used to provide flexibility to a numerical range endpoint by providing that a given value may be "a little above" or "a little below" the endpoint without affecting the desired result. Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

It is understood that aspects and embodiments of the invention described herein include "comprising," "consisting," and "consisting essentially of" aspects and embodiments. For all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the condition being treated, but do not contain any other components which substantially affect the condition being treated other than those components expressly listed; or, if the composition does contain extra components other than those listed which substantially affect the condition being treated, the composition does not contain a sufficient concentration or amount of the extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed. As a non-limiting specific example, when a composition is described as 'consisting essentially of' a component, the composition may additionally contain any amount of pharmaceutically acceptable carriers, vehicles, or diluents and other such components which do not substantially affect the condition being treated.

As used in the specification, the phrase "any of the embodiments" means the same as "some of the embodiments." The aspects of the embodied method elements are not meant to be limiting and can be combined with any or all of the different embodiments exemplified herein.

As used in the specification and the appended claims, the singular forms "a," "an," and "the" include plural referents unless the context clearly indicates otherwise.

General Techniques

Unless defined otherwise, technical and scientific terms used herein have the same meaning as commonly understood by one of ordinary skill in the art to which this invention belongs.

The practice of the present invention will employ, unless otherwise indicated, conventional techniques of protein biology, protein chemistry, molecular biology (including recombinant techniques), microbiology, cell biology, biochemistry, and immunology, which are within the skill of the art. Such techniques are explained fully in the literature, such as "Molecular Cloning: A Laboratory Manual", second edition (Sambrook et al., 1989); "Current Protocols in Molecular Biology" (Ausubel et al., eds., 1987, periodic updates); "PCR: The Polymerase Chain Reaction", (Mullis et al., eds., 1994); and Singleton et al., *Dictionary of Microbiology and Molecular Biology,* 2nd ed., J. Wiley & Sons (New York, N.Y. 1994).

Allograft Recipients

The allograft recipient may be of any age. In some embodiments, the individual is a child. In one embodiment, the child is an infant. In another embodiment, the child is a toddler. In other embodiments, the individual is a young adult under the age of 23. In some embodiments, the individual is approximately 1, 2, 3, 4, 5, 6, 7, 8, 9, 10, 11, 12, 13, 14, 15, 16, 17, 18, 19, 20, 21, or 22 years of age. In some embodiments, the individual is an adult over the age of 23. In some embodiments, the individual is approximately 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 67, 68, 69, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 years of age. In one embodiment, the allograft recipient is female. In another embodiment, the allograft recipient is male.

The transplant operation/surgery may take place at a specially-designated treatment facility or transplant center. The transplant center may be located anywhere in the world. In one embodiment, the transplant center is in the United States of America Collection and Processing of Biological Samples A biological sample is collected from an individual who has received an allograft transplant. In some embodiments, the allograft recipient has no outward symptoms of AR. In other embodiments, the allograft recipient shows symptoms of AR. Any type of biological sample may be collected, including but not limited to whole blood, blood, serum, plasma, urine, mucus, saliva, cerebrospinal fluid, tissues, biopsies and combinations thereof. In one embodiment, the biological sample is whole blood. In another embodiment, the biological sample is blood. In one embodiment, the sample is blood serum. In one aspect, the sample is blood serum from a donor. In another aspect, the sample is blood serum from a recipient. In some embodiments, the blood sample is peripheral blood. In another embodiment, the biological sample is peripheral blood mononuclear cells. In some embodiments, the biological sample is peripheral blood lymphocytes. In some embodiments, the biological sample is a tissue biopsy.

Collection of a biological sample from an allograft recipient can occur at any time before or after receiving an organ transplant. In some embodiments, the biological sample is collected during routine protocol surveillance examination. In other embodiments, the biological sample is collected when a treating clinician has reason to suspect that the individual is undergoing an AR response.

The biological sample that is collected from an allograft recipient may be paired with contemporaneous allograft biopsies from the same patient when creating a reference for AR or no-AR samples. Typically, the allograft biopsy is collected from the recipient within 48 hours of the biological sample collection.

In some embodiments, blood is collected from an organ transplant donor and an organ transplant recipient. In some embodiments, blood is collected from an organ transplant recipient. In some aspects, the blood is collected in a suitable vessel (e.g., a vacutainer or syringe) containing an anti-coagulant (e.g., sodium citrate or EDTA). In some embodiments, about 1 mL to about 100 mL of blood is collected, including all integers within the specified range. In some aspects, about 5 mL, about 10 mL, about 15 mL, about 20 mL, about 25 mL, about 30 mL, about 35 mL, about 40 mL, about 45 mL, about 50 mL, about 55 mL, about 60 mL, about 65 mL, about 70 mL, about 75 mL, about 80 mL, about 85 mL, about 90 mL, about 95 mL, or about 100 mL of blood is collected.

In some embodiments described herein, peripheral blood mononuclear cells (PBMCs) may be isolated from whole blood by ficoll centrifugation methods known in the art. In some aspects, PBMCs are isolated and endothelial cells are grown out from endothelial progenitor cells (EPCs) as a stable primary endothelial culture as is known in the art see, for example, Asahara, T. et al. *Science* 1997, 275, 964-967 and U.S. Pat. No. 8,492,148, each of which is incorporated by reference herein for their teachings thereof.

In some aspects, a tissue biopsy is also collected at the time of engraftment. In other embodiments, the biopsy is collected up to 24 months post-transplantation. In one embodiment, the biopsy may be collected at about 3 months post-transplantation; at about 6 months post-transplantation; at about 12 months post-transplantation; at about 18 months post-transplantation; or at about 24 months post-transplantation. These time points should not be seen as limiting, as a biopsy and/or biological sample may be collected at any point following transplantation. Rather, these time points are provided to demonstrate periods following transplantation when routine surveillance is most likely to occur in a majority of allograft recipients. In addition, these time points demonstrate periods following transplantation when an AR response is most likely to occur.

In some aspects, kidney allograft biopsies that are collected may be scored according to the Banff classification system (Solez, K. et al. *Am. J. Transplant.*, 2008, 8, 753-760; Mengel, M. et al. *Am. J. Transplant.* 2012, 12, 563-570). This system classifies the observed pathology of a renal organ biopsy sample as normal histology, hyperacute rejection, borderline changes, acute rejection, chronic allograft nephropathy, and other changes. The Banff classification sets standards in renal transplant pathology and is widely used in international clinical trials of new anti-rejection agents. As described herein, "acute rejection" (AR) is defined for biopsy samples with a Banff tubulitis score (t) of less than or equal to 1 and an interstitial infiltrate score of less than or equal to 0; "Stable" ("STA")/"no-AR" is defined for biopsy samples displaying an absence of AR (no-AR) or any other substantial pathology; and "Other" is defined for samples displaying an absence of Banff-graded AR, but either meet the Banff criteria for chronic allograft injury, chronic calcineurin inhibitor toxicity, BK viral infection, or other graft injury.

In some embodiments described herein, endothelial cells are used for the identification of anti-endothelial cell antibodies. Endothelial cells may be isolated from a plurality of cells by contacting the mixture of cells with an endothelial cell isolation reagent to form an endothelial cell-isolation reagent complex, see, for example, U.S. Pat. No. 8,034,635, which is incorporated by reference herein for its teachings thereof. The complex is formed via a specific affinity interaction between the isolation reagent and the cell. The complex may then be separated from the mixture to isolate the endothelial cell. The complex may be separated from the mixture using techniques known in the art, such as by, for example, flow cytometry (FACS) or use of a magnetic field. Alternatively, the complex may be separated from the mixture by attaching the endothelial cell isolation reagent to a solid support as described herein. Additional washing step may be employed by re-suspending the complex in a biologically compatible solution. The complex can be re-suspended (e.g., washed as many times as needed). A biologically compatible solution comprises biological buffers known in the art such as phosphate buffer saline (PBS).

In some embodiments, the endothelial cell isolation reagent may be any reagent that specifically identifies an endothelial cell and can be further isolated using methods and techniques known in the art and exemplified herein. For example, the endothelial cell isolation reagent may comprise a ligand for an endothelial cell surface receptor. Non-limiting endothelial cell surface receptors may include, for example, the EC-specific tyrosine kinase receptor Tie-2 or VEGFR and the ligand may include angiopoietin, VEGF, or an antibody specific for the cell surface receptor. The antibody may be any monoclonal antibody or polyclonal antibody. Reference to antibodies encompasses not only an intact antibody but also an immunologically-active antibody fragment (e.g., a Fab or (Fab)2 fragment; an engineered single chain Fv molecule; or a chimeric molecule, e.g., an antibody which contains the binding specificity of one antibody, e.g., of murine origin, and the remaining portions of another antibody, e.g., of human origin. Thus, in some aspects, the endothelial cell isolation reagent may comprise a monoclonal antibody with specificity to Tie-2 or VEGFR-1.

In some embodiments, the endothelial cell isolation reagent may be attached to a solid support. Non-limiting and exemplary solid supports may comprise a particle, a polymer (e.g., polystyrene, polyethylene), a vessel, a chamber, a dipstick, beads, particles, membranes (e.g., nylon, nitrocellulose or polyvinylidenefluoride (PVDF)), or other forms known in the art. The solid support may carry functional groups such as hydroxyl, carboxyl, aldehyde or amino groups. The solid support may be positively charged, negatively charged or hydrophobic. Functionalized coated supports may be prepared by modification of the support. For example, an uncoated support is treated with a polymer carrying one or such functional groups, such as polyurethane together with a polyglycol to provide hydroxyl groups, or a cellulose derivative to provide hydroxyl groups, a polymer or copolymer of acrylic acid or methacrylic acid to provide carboxyl groups, or an aminoalkylated polymer to provide amino groups. U.S. Pat. No. 4,654,267 describes the introduction of many surface coatings and is incorporated by reference herein for its teachings thereof.

Exemplary and useful particles may be made of metal compounds, silica, latex, polymeric material, or a silica, latex or polymer nuclei coated with a metal or metal compound, such as iron, gadolinium, zinc, indium, gold, silver, cobalt, copper, or magnesium and may be magnetizable or magnetic. By "magnetizable or magnetic" is meant that the particle is capable of having a magnetic moment impaired to it when it is placed in a magnetic field.

The endothelial cell isolation reagent may be labeled with a detectable marker. For example, the endothelial cell isolation reagent may be labeled with a radioactive isotope (e.g., 1251, and 1311), enzymes (e.g., peroxidase, beta.-galactosidase, alkaline phosphatase) or fluorescent substances (e.g., fluorescein isothiocyanate (FITC). The labels on the detection reagent may be quantified by conventional methods well-known in the art to quantify the formed immune complex (e.g., an ELISA or other solid-phase immunoassay). The mixture of cells may comprise any sample known to or suspected of containing an endothelial cell. For example the mixture may be a biological sample such as whole blood, sera, leucapherisate, bone marrow, peripheral blood mononuclear cells or a tissue homogenate.

In some embodiments, the endothelial cell may comprise any cell derived from any part of the vasculature as described herein. For example, the endothelial cell may originate from large and small veins and arteries capillaries, the umbilical vein of newborns, blood vessels in the brain or from vascularized solid tumors. The endothelial cell may comprise a mature cell or alternatively an endothelial precursor cell. In some aspects, the endothelial cell may be Tie-2 positive.

Evaluation of Gene Expression in Biological Samples

Biological samples taken from an allograft recipient can be used to evaluate the level of genes which are differentially expressed in individuals undergoing an AR response. Various techniques of measuring gene expression are known to one of skill in the art. One non-limiting method is to extract RNA from the collected biological sample and to synthesize cDNA. The cDNA can then be amplified using primers or labeled primers specific for the target genes (i.e., genes which are differentially expressed in individuals undergoing an AR response) and subsequently analyzed using quantitative polymerase chain reaction (qPCR). qPCR platforms such as BioMark (Fluidigm, South San Francisco, Calif.) or ABI viia7 (Life Technologies, Foster City, Calif.) may be used.

In some embodiments, one of either the gene specific primers or dNTPs may be labeled such that the synthesized cDNAs are labeled. By labeled it is meant that the entities comprise a member of a signal producing system and are thus detectable, either directly or through combined action with one or more additional members of a signal producing system. Examples of directly detectable labels include isotopic and fluorescent moieties incorporated into, usually covalently bonded to, a nucleotide monomeric unit, e.g., dNTP or monomeric unit of the primer. Isotopic moieties or labels of interest include 32 P, 33 P, 35 S, 125 I, and the like. Fluorescent moieties or labels of interest include coumarin and its derivatives, e.g., 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. Quantum Dye™, fluorescent energy transfer dyes, such as thiazole orange-ethidium heterodimer, TOTAB, etc. Labels may also be members of a signal producing system that act in concert with one or more additional members of the same system to provide a detectable signal. Illustrative examples of such labels are members of a specific binding pair, such as ligands, e.g., biotin, fluorescein, digoxigenin, polyvalent cations, chelator groups and the like, wherein the members specifically bind to additional members of the signal producing system, wherein the additional members provide a detectable signal either directly or indirectly, e.g., antibody conjugated to a fluorescent moiety or an enzymatic moiety capable of converting a substrate to a chromogenic product, e.g., alkaline phosphatase conjugate antibody and the like. Labeled nucleic acid can also be produced by carrying out PCR in the presence of labeled primers. U.S. Pat. No. 5,994,076 is incorporated by reference solely for its teachings of modified primers and dNTPs thereof.

Another non-limiting method of measuring gene expression is northern blotting. The gene expression level of genes that encode proteins can also be determined using protein quantification methods such as western blotting. Use of proteomic assays to measure the level of differentially expressed genes is also embraced herein. A person of skill in the art would know how to use standard proteomic assays in order to measure the level of gene expression.

Methods for Detecting and Isolating Anti-Endothelial Cell Antibodies

In some embodiments described herein are methods for detecting and isolating anti-endothelial cell antibodies. It was found that the presence or absence of anti-endothelial cell antibodies, and in some aspects, a specific set of anti-endothelial cell antibodies is useful for the diagnosis or prediction of an organ transplant recipient as having an allograft rejection.

In some embodiments, anti-endothelial cell antibodies are detected after a cell-based assay, such as a cross-match test. In some aspects, the cross-match test comprises mixing a donor endothelial cell and recipient serum. In this way, cross-matching detects those antigenic differences to which the recipient is already sensitized. Thus, in some aspects, a donor is crossmatched to a recipient by first contacting a donor sample with an endothelial cell isolation reagent as described herein to isolate an endothelial cell and then contacting the recipient sample with the isolated endothelial cell. The reactivity of the recipient sample with the isolated endothelial cell is then determined. By "reactivity" it is meant that that a complex is formed via a specific affinity interaction between a component of the recipient sample (e.g., an antibody) and the isolated donor endothelial cell.

In some aspects, the specific affinity interaction comprises an antibody and antigen complex. In some aspects, the antibody is already present in the recipient sera and forms a complex with an antigen present in the donor sample. In some aspects, the antigen is present on a donor endothelial cell present within the sample; when the antibody is present in the recipient sera, it forms a specific affinity interaction with the donor endothelial cell. Thus, no reactivity of the recipient sample with the isolated endothelial cell indicates compatibility between the donor and recipient sample. In contrast, reactivity of the recipient sample with the isolated endothelial cell indicates non-compatibility between the donor and recipient sample. Compatibility is measured by no or low hyperacute rejection of the donor transplant by the recipient.

In some embodiments, the donor and the recipient are, e.g., any mammal; e g, a human, a pig, a cow, a dog, a feline or a horse. In some aspects, the donor and the recipient are the same species. Alternatively, in other aspects, the donor and the recipient are of different species.

In some embodiments, the donor sample comprises whole blood, sera, leucapherisate, bone marrow, peripheral blood mononuclear cells or a tissue homogenate. In some aspects, donor sample comprises an endothelial cell (e.g., an endothelial progenitor cell) from whole blood, sera, leucapherisate, bone marrow, peripheral blood mononuclear cells or a tissue homogenate. In some embodiments, the recipient sample comprises whole blood, sera, leucapherisate, bone marrow, peripheral blood mononuclear cells or a tissue homogenate. In some aspects, the samples are subjected to a pre-purification step prior to crossmatching known in the art.

Reactivity is determined by methods known in the art. For example, reactivity is measured by methods known in the art, such as a solid-phase immunoassay (e.g., an ELISA assay), flow cytometry (e.g., a flow cytometric cross-match assay), or a complement-dependent lymphotoxicity cross-match (CDC cross-match assay).

In some embodiments, the anti-endothelial cell antibodies originating from the recipient or recipient immune cells are isolated by methods known in the art. In some aspects, at least one anti-endothelial cell antibody is isolated following an endothelial cell cross-match test, as described herein. In one aspect, at least one anti-endothelial cell antibody is bound to a donor derived endothelial cell in the cross-match test. In another aspect, the at least one anti-endothelial cell antibody is acid eluted and neutralized from the donor endothelial cell by methods known in the art see, for example, Lucchiari, N. et al. *Hum Immunol* 2000, 61, 518-527, which is incorporated by reference herein for its teachings thereof. In another aspect, the eluted and neutralized anti-endothelial cell antibodies are stored for identification and further testing.

In some embodiments described herein, at least one or more anti-endothelial cell antibodies or a mixture of anti-endothelial cell antibodies may be identified using a protein array (e.g., a peptide antigen array). In some aspects, described herein, the mixture of anti-endothelial cell antibodies may be obtained using antibody isolation methods following an endothelial cell cross match test as described herein. In some aspects the protein array has a plurality of proteins or peptides or a combination of proteins and peptides attached to a solid substrate described herein. In one aspect, individual human peptides are N-terminal GST fusion proteins spotted onto a nitrocellulose-coated glass slides. The immobilized peptides are useful for specifically isolating a mixture of anti-endothelial cell antibodies from a sample, wherein the mixture of anti-endothelial cell antibodies may demonstrate an affinity for one or more of the immobilized peptides. In this way, the antigenic reactivity (or target) of each anti-endothelial cell antibody may be identified. The peptides may number from about 1 peptide to about 35,000 known peptides depending on the breadth of antigenic target coverage desired. In one aspect about 9,500 peptides are tested using the methods described herein.

As described above, the peptides interact specifically with an anti-endothelial cell antibody having an affinity for one or more peptides immobilizing and binding the anti-endothelial cell antibody onto the solid substrate. In some aspects, the presence of an anti-endothelial cell antibody bound to a peptide on the solid substrate is detected with a class specific secondary antibody (e.g., a class specific secondary antibody; anti-human IgG, IgM, IgA.). In some aspects, the class specific secondary antibody is further labelled with a detectable label. Detectable label quantitation may be assessed using any imaging and quantitation method known in the art. See, for example, U.S. Patent Application Pub No. US2006/0281134, which is incorporated by reference herein for its specific teachings of peptide arrays and subsequent quantitation thereof.

In some aspects, the anti-endothelial cell antibody is isolated by antibody isolation methods. Non-limiting examples of antibody isolation methods include antibody precipitation methods (e.g., precipitation with ammonium sulfate, octonic acid, polyethylene glycol, ethacridine); dialysis; size exclusion chromatography (e.g., gel filtration chromatography); ion exchange chromatography, immobilized metal chelate chromatography; thiophilic adsorption; melon gel chromatography; epitope based isolation methods (e.g., protein A, protein G, or protein L immobilized on a resin or agarose); isolation of IgM antibodies with mannan binding protein; isolation of IgA antibodies with jacalin lectin; isolation using antibody capture beads (e.g., protein A, protein G, protein L, MBP, or jacalin lectin immobilized on a magnetic beads, bead resin, sepharose beads, or agarose beads), an affinity column (e.g., protein A, protein G, protein L, MBP, or jacalin lectin immobilized on an affinity column).

In some embodiments, the anti-endothelial cell antibody is captured with a capture element. In some aspects, the capture element selectively is bound by the anti-endothelial cell antibody; therefore, the capture element can be any antibody binding element. In some aspects, the capture element is an antigen to one or more anti-endothelial cell antibodies. Non-limiting exemplary capture elements include a full length protein, a protein fragment, a peptide, a polypeptide, a polypeptide fragment, an antibody, an antibody fragment, an antibody binding domain, an antigen, an antigen fragment, an antigenic determinant, an epitope, a hapten, an immunogen, an immunogen fragment, a metal ion, a metal ion-coated molecule, biotin, avidin, streptavidin, an inhibitor, a co-factor, a substrate, an enzyme, a receptor, a receptor fragment, a receptor subunit, a receptor subunit fragment, a ligand, a receptor ligand, a receptor agonist, a receptor antagonist, a signalling molecule, a signalling protein, a signalling protein fragment, a growth factor, a growth factor fragment, a transcription factor, a transcription factor fragment, an inhibitor, a monosaccharide, an oligosaccharide, a polysaccharide, a glycoprotein, a lipid, a cell, a cell-surface protein, a cell-surface lipid, a cell-surface carbohydrate, a cell-surface glycoprotein, a cell extract, a virus, a virus coat protein, a hormone, a serum protein, a milk protein, an oligonucleotide, a macromolecule, or any combination thereof.

In some embodiments, the capture element is a full length protein, a protein fragment, a peptide, a polypeptide, or a polypeptide fragment. In some embodiments, the capture element is a peptide. In some aspects, each individual peptide is artifically synthesized and is optimized for forming an affinity interaction with an anti-endothelial cell antibody described herein. In one aspect, the peptide or protein fragment is modified with an isolation tag. In one aspect, the isolation tag is any chemical modification or addition of an amino acid sequence tag that allows for the isolation of a protein fragment or peptide. In another aspect, the modification to the peptide includes the addition of an isolation tag including biotin, a GST tag, an amide group, or a streptavidin tag.

In some embodiments, one or more capture elements (e.g., one or more peptides) is mixed with a complex biological solution (e.g., a sample from a subject) potentially comprising one or more anti-endothelial cell antibodies to form an affinity reaction. As described herein, the capture element may further comprise an isolation tag (e.g., a biotin or GST tag) for the subsequent purification of the antibody/capture element complex for further detection and quantification as described herein.

In one embodiment, test recipient sera are used to test the activation state of a pre-established culture of test endothelial cells. Accordingly, the serum of a potential recipient that is reactive to a donor organ having anti-endothelial cell antibodies will activate an established culture of endothelial cells; whereas a non-reactive serum not having anti-endothelial cell antibodies will not activate an established culture of endothelial cells.

In another embodiment, isolated anti-endothelial cell antibodies from a recipient sera can be used for testing the activation state of a pre-established culture of test endothelial cells. In one aspect, the isolated anti-endothelial cell antibodies are isolated following an endothelial cell cross-match test between a donor and recipient by the methods described herein. In another aspect, the anti-endothelial cell antibodies are isolated by any antibody isolation method described herein. Accordingly, the isolated anti-endothelial cell antibody eluate derived from a recipient that is reactive to a donor organ will activate an established culture of endothelial cells; whereas a non-reactive serum will not activate an established culture of endothelial cells.

In some embodiments, the activation state of an endothelial cell following stimulation with an anti-endothelial cell antibody can be determined by measuring an increase or decrease in the gene expression or protein level of at least one or more endothelial activation markers. In some embodiments, the measurement of an increased level, decreased level, or combination of increased or decreased levels of one or more endothelial activation markers following stimulation with an endothelial cell antibody defines an anti-endothelial cell antibody endothelial activation signature. In one aspect, the endothelial activation markers increased include a cell surface protein comprising a HLA class I gene and E selectin, PECAM1, and ICAM1 cell adhesion molecules. In another aspect, the endothelial cell activation marker includes at least one or more or of a combination of inflammatory cytokines from Table 4. The inflammatory cytokines indicating the activation state of an endothelial cell may number at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, or at least 54 of the inflammatory cytokines listed in Table 4. In another aspect, the endothelial cell activation signature includes increased levels of the PDGF, RANTES (i.e., CCL5), and RESISTIN. In another aspect, the endothelial cell activation signature includes the decreased level of CCL3, CCL4, CXCL5, and CXCL.

In some aspects, one or more of the endothelial cell activation markers described herein is measured by a qualitative measurement, semi-quantitative or highly quantitative measurement methods. Exemplary, non-limiting methods include, immunohistochemistry, immunofluorescence, flow cytometry, ELISA, western blotting, PCR, qRT-PCR, and microarrays.

The established culture of endothelial cells may be any diseased or normal primary endothelial cell. For example, the endothelial cell may be an endothelial progenitor cell, any ex vivo whole tissue culture comprising endothelial cells, or any immortalized endothelial cell, or a mixture of endothelial cells thereof.

The test endothelial cell may be from any mammal (e.g., a human, mouse, or rat). Exemplary non-limiting examples of human endothelial cultures comprise human umbilical vein endothelial cells (HUVECs), human cardiac endothelial cells, human bladder endothelial cells, human uterine MV endothelial cells, human dermal microvascular endothelial cells, human lunch microvascular endothelial cells (HMVEC-L), human aortic endothelial cells, human cardiac microvascular endothelial cells, human coronary artery endothelial cells, or human pulmonary artery endothelial cells. In some aspects, the test endothelial cell described herein may be derived from a recipient donor or donor organ. In other aspects, the test endothelial cell may be purchased from a commercial vendor.

Detection of Anti-Endothelial Cell Antibodies and HLA Antibodies Using Solid-Phase Immunoassays In some embodiments described herein, one or more anti-endothelial cell antibodies can be measured in a solid-phase immunoassay (e.g., ELISA or surface plasmon resonance). In some aspects, the solid-phase immunoassay comprises an enzyme-linked immunosorbent assay (ELISA). In some aspects, the solid-phase immunoassay comprises isolating anti-endothelial cell antibodies from a recipient blood sample or sera with an antibody capture element and measuring the level of the isolated anti-endothelial cell antibodies.

In some embodiments, the solid phase immunoassay comprises one or more solid supports. In some aspects, the surface of solid supports may be solid or porous and of any convenient shape. Non-limiting examples of suitable insoluble supports to which the protein, a protein fragment, a peptide, a polypeptide, or a polypeptide fragment is bound to include beads, membranes, solid plates, gold plates, and microtiter plates. These are typically made of a metal, glass, plastic (e.g. polystyrene), polysaccharides, nylon or nitrocellulose. Microtiter plates are especially convenient because a large number of assays can be carried out simultaneously, using small amounts of reagents and samples. In some aspects, the microtiter plate comprises 96 individual wells. In some aspects, the microtiter plate comprises 384 individual wells.

In some aspects, the solid support may be further modified with specific coatings for binding the protein, a protein fragment, a peptide, a polypeptide, or a polypeptide fragment. Non-limiting examples of solid support coatings include biotin, deglycosylated avidin, avidin, streptavidin, nickel, copper, glutathione, anti-GST (e.g., a monoclonal antibody specific to GST tags), protein A, protein G, protein L, antigen specific secondary antibodies, maleic anhydride, or maleimide. The protein, a protein fragment, a peptide, a polypeptide, or polypeptide fragments described herein can be linked to the solid support by methods known in the art. Exemplary non-limiting linking methods include, biotinylation, GST tagging, amidation, or streptavidin tagging.

In some embodiments described herein are antibody capture elements comprising a solid substrates and one or more full length protein, protein fragment, peptide, polypeptide, recombinant peptide, recombinant protein, or a polypeptide fragments. In some aspects further described herein, the one or more one or more full length protein, protein fragment, peptide, polypeptide, recombinant peptide, recombinant protein, or a polypeptide fragments may be linked or attached to the solid substrates described herein. In some aspects, the one or more full length protein, protein fragment, peptide, polypeptide, recombinant peptide, recombinant protein, or a polypeptide fragments may be used to capture one or more antibodies in a free solution and the complex may then be bound to a solid substrate as described herein.

In one embodiment, the antibody capture element in the solid-phase immunoassay comprises a solid substrate comprising an antibody capture bead. In one aspect, the antibody capture bead is a magnetic bead, bead resin, or sepharose bead. In another aspect, the antibody capture bead is further linked to a protein, a protein fragment, a peptide, a polypeptide, or a polypeptide fragment. In some aspects, one full length protein, a protein fragment, a peptide, a polypeptide, recombinant peptide, recombinant protein, or a polypeptide fragment is linked to one capture bead. In some aspects, more than one (e.g., 1, 2, 3, 4, 5, or more) full length protein, a protein fragment, a peptide, a polypeptide, recombinant peptide, recombinant protein, or a polypeptide fragment is linked to one capture bead. The full length protein, a protein fragment, a peptide, a polypeptide, recombinant peptide, recombinant protein, or a polypeptide fragment is able to form a specific affinity interaction to at least one anti-endothelial cell antibody. In this way, the antibody capture bead interacts specifically with an anti-endothelial cell antibody present in a sample and provides a method for isolating the anti-endothelial cell antibody from all other antibodies (e.g., including HLA antibodies) and other biological materials in a sample. Methods for using antibody capture beads are well known in the art and may comprise additional washing, centrifuging, and other purification steps. In some aspects, the antibody capture bead may be embedded in a solid support structure or may be free floating.

In another embodiment, the antibody capture element in the solid-phase immunoassay comprises a plate. In one aspect, the plate is a microtiter plate. In another aspect, the microtiter plate is further linked to a protein, a protein fragment, a peptide, a polypeptide, or a polypeptide fragment. In some aspects, one type (e.g., a plurality of the same type) of full length protein, a protein fragment, a peptide, a polypeptide, recombinant peptide, recombinant protein, or a polypeptide fragment is linked to one well of the microtiter plate. In some aspects, more than one (e.g., 1, 2, 3, 4, 5, or more) full length protein, a protein fragment, a peptide, a polypeptide, recombinant peptide, recombinant protein, or a polypeptide fragment is linked to adjacent wells in a microtiter plate. The full length protein, a protein fragment, a peptide, a polypeptide, recombinant peptide, recombinant protein, or a polypeptide fragment is able to form a specific affinity interaction to at least one anti-endothelial cell antibody. In this way, the microtiter plate interacts specifically with an anti-endothelial cell antibody present in a sample and provides a method for isolating the anti-endothelial cell antibody from all other antibodies (e.g., including HLA antibodies) and other biological materials in a sample. Methods for using microtiter plates and linking proteins or peptides to microtiter plates are known in the art and may comprise additional washing, centrifuging, and other purification steps.

In another aspect, the plate is coated with a protein binding coating. The plate may be a solid plate or microtiter plate. In some aspects, the plate is coated with streptavidin. Thus, the plate interacts specifically with any streptavidin binding element (e.g., biotin). In some aspects, a protein fragment, a peptide, a polypeptide, recombinant peptide, recombinant protein, or a polypeptide fragment is biotinylated. The full length protein, a protein fragment, a peptide, a polypeptide, recombinant peptide, recombinant protein, or a polypeptide fragment is able to form a specific affinity interaction to at least one anti-endothelial cell antibody. In this way, the microtiter plate interacts specifically with a biotinylated protein fragment, a peptide, a polypeptide, recombinant peptide, recombinant protein, or a polypeptide fragment that further forms an affinity interaction with an anti-endothelial cell antibody present in a sample and provides a method for isolating the anti-endothelial cell antibody from all other antibodies (e.g., including HLA antibodies) and other biological materials in a sample. Methods for coating plates with streptavidin are well known in the art and may comprise additional washing, centrifuging, and other purification steps.

In some embodiments described herein, the antibody capture element in the solid-phase immunoassay comprises a full length protein, protein fragment, peptide, polypeptide, recombinant peptide, recombinant protein, or a polypeptide fragment corresponding to at least a portion or peptide fragment of one gene product (protein) listed in Table 2. In some aspects, the full length protein, the protein fragment, peptide, polypeptide, recombinant peptide, recombinant protein, or a polypeptide fragment comprises a portion or peptide fragment of the amino acid sequence of any of the proteins listed in Table 2. In some aspects, the size of the protein fragment, peptide, polypeptide, recombinant peptide, recombinant protein, or a polypeptide fragment corresponding to any of the proteins listed in Table 2 may be at least about 1 to at least about 3,000 amino acids in length. The size of the protein fragment, peptide, polypeptide, recombinant peptide, recombinant protein, or a polypeptide fragment maybe a portion or peptide fragment of any of the proteins corresponding to any of the proteins listed in Table 2 wherein the portion or peptide fragment may be at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 101, at least 102, at least 103, at least 104, at least 105, at least 106, at least 107, at least 108, at least 109, at least 110, at least 111, at least 112, at least 113, at least 114, at least 115, at least 116, at least 117, at least 118, at least 119, at least 120, at least 121, at least 122, at least 123, at least 124, at least 125, at least 126, at least 127, at least 128, at least 129, at least 130, at least 131, at least 132, at least 133, at least 134, at least 135, at least 136, at least 137, at least 138, at least 139, at least 140, at least 141, at least 142, at least 143, at least 144, at least 145, at least 146, at least 147, at least 148, at least 149, at least 150, at least 151, at least 152, at least 153, at least 154, at least 155, at least 156, at least 157, at least 158, at least 159, at least 160, at least 161, at least 162, at least 163, at least 164, at least 165, at least 166, at least 167, at least 168, at least 169, at least 170, at least 171, at least 172, at least 173, at least 174, at least 175, at least 176, at least 177, at least 178, at least 179, at least 180, at least 181, at least 182, at least 183, at least 184, at least 185, at least 186, at least 187, at least 188, at least 189, at least 190, at least 191, at least 192, at least 193, at least 194, at least 195, at least 196, at least 197, at least 198, at least 199, at least 200, at least 201, at least 202, at least 203, at least 204, at least 205, at least 206, at least 207, at least 208, at least 209, at least 210, at least 211, at least 212, at least 213, at least 214, at least 215, at least 216, at least 217, at least 218, at least 219, at least 220, at least 221, at least 222, at least 223, at least 224, at least 225, at least 226, at least 227, at least 228, at least 229, at least 230, at least 231, at least 232, at least 233, at least 234, at least 235, at least 236, at least 237, at least 238, at least 239, at least 240, at least 241, at least 242, at least 243, at least 244, at least 245, at least 246, at least 247, at least 248, at least 249, at least 250, at least 251, at least 252, at least 253, at least 254, at least 255, at least 256, at least 257, at least 258, at least 259, at least 260, at least 261, at least 262, at least 263, at least 264, at least 265, at least 266, at least 267, at least 268, at least 269, at least 270, at least 271, at least 272, at least 273, at least 274, at least 275, at least 276, at least 277, at least 278, at least 279, at least 280, at least 281, at least 282, at least 283, at least 284, at least 285, at least 286, at least 287, at least 288, at least 289, at least 290, at least 291, at least 292, at least 293, at least 294, at least 295, at least 296, at least 297, at least 298, at least 299, at least 300, at least 301, at least 302, at least 303, at least 304, at least 305, at least 306, at least 307, at least 308, at least 309, at least 310, at least 311, at least 312, at least 313, at least 314, at least 315, at least 316, at least 317, at least 318, at least 319, at least 320, at least 321, at least 322, at least 323, at least 324, at least 325, at least 326, at least 327, at least 328, at least 329, at least 330, at least 331, at least 332, at least 333, at least 334, at least 335, at least 336, at least 337, at least 338, at least 339, at least 340, at least 341, at least 342, at least 343, at least 344, at least 345, at least 346, at least 347, at least 348, at least 349, at least 350, at least 351, at least 352, at least 353, at least 354, at least 355, at least 356, at least 357, at least 358, at least 359, at least 360, at least 361, at least 362, at least 363, at least 364, at least 365, at least 366, at least 367, at least 368, at least 369, at least 370, at least 371, at least 372, at least 373, at least 374, at least 375, at least 376, at least 377, at least 378, at least 379, at least 380, at least 381, at least 382, at least 383, at least 384, at least 385, at least 386, at least 387, at least 388, at least 389, at least 390, at least 391, at least 392, at least 393, at least 394, at least 395, at least 396, at least 397, at least 398, at least 399, at least 400, at least 401, at least 402, at least 403, at least 404, at least 405, at least 406, at least 407, at least 408, at least 409, at least 410, at least 411, at least 412, at least 413, at least 414, at least 415, at least 416, at least 417, at least 418, at least 419, at least 420, at least 421, at least 422, at least 423, at least 424, at least 425, at least 426, at least 427, at least 428, at least 429, at least 430, at least 431, at least 432, at least 433, at least 434, at least 435, at least 436, at least 437, at least 438, at least 439, at least 440, at least 441, at least 442, at least 443, at least 444, at least 445, at least 446, at least 447, at least 448, at least 449, at least 450, at least 451, at least 452, at least 453, at least 454, at least 455, at least 456, at least 457, at least 458, at least 459, at least 460, at least 461, at least 462, at least 463, at least 464, at least 465, at least 466, at least 467, at least 468, at least 469, at least 470, at least 471, at least 472, at least 473, at least 474, at least 475, at least 476, at least 477, at least 478, at least 479, at least 480, at least 481, at least 482, at least 483, at least 484, at least 485, at least 486, at least 487, at least 488, at least 489, at least 490, at least 491, at least 492, at least 493, at least 494, at least 495, at least 496, at least 497, at least 498, at least 499, at least 500, at least about 525, at least about 550, at least about 575, at least about 600, at least about 625, at least about 650, at least about 675, at least about 700, at least about 725, at least about 750, at least about 775, at least about 800, at least about 825, at least about 850, at least about 875, at least about 900, at least about 925, at least about 950, at least about 975, at least about 1000, at least about 1025, at least about 1050, at least about 1075, at least about 1100, at least about 1125, at least about 1150, at least about 1175, at least about 1200, at least about 1225, at least about 1250, at least about 1275, at least about 1300, at least about 1325, at least about 1350, at least about 1375, at least about 1400, at least about 1425, at least about 1450, at least about 1475, at least about 1500, at least about 1550, at least about 1600, at least about 1650, at least about 1700, at least about 1750, at least about 1800, at least about 1850, at least about 1900, at least about 1950, at least about 2000, at least about 2050, at least about 2100, at least about 2150, at least about 2200, at least about 2250, at least about 2300, at least about 2350, at least about 2400, at least about 2450, at least about 2500, at least about 2550, at least about 2600, at least about 2650, at least about 2700, at least about 2750, at least about 2800, at least about 2850, at least about 2900, at least about 2950, or at least about 3000 amino acids. In some aspects, the protein fragment, peptide, polypeptide, recombinant peptide, recombinant protein, or a polypeptide fragment corresponding to at least a portion or peptide fragment of the proteins listed in Table 2 may be additionally modified to include one or more tags comprising biotin tag, a GST tag, an amide group, or a streptavidin tag or a combination thereof.

In some embodiments, the full length protein, protein fragment, peptide, polypeptide, recombinant peptide, recombinant protein, or a polypeptide fragment corresponds to at least a portion or peptide fragment of one protein listed in Table 2. In some aspects, the full length protein, protein fragment, peptide, polypeptide, recombinant peptide, recombinant protein, or a polypeptide fragment corresponds to at least a portion or peptide fragment of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, or at least 55 proteins listed in Table 2. In some aspects, the full length protein, a protein fragment, a peptide, a polypeptide, recombinant peptide, recombinant protein, or a polypeptide fragment corresponds to at least a portion or fragment of endoglin, Fms-like tyrosine kinase-3 (FLT3) ligand, EGF-like repeats and discoidin I-like domains 3 (EDIL3) and intercellular adhesion molecule 4 (ICAM4).

In some embodiments described herein is a method for detecting anti-endothelial cell antibodies in allograft rejection. In some aspects described herein is a solid-phase immunoassay for detecting at least one or more anti-endothelial cell antibodies. In some aspects, the steps of performing the solid-phase immunoassay comprises: isolating at least one or more anti-endothelial cell antibodies with an antibody capture element or antibody isolation method described herein; measuring the level of at least one or more anti-endothelial cell antibodies; comparing the level of at least one or more anti-endothelial cell antibodies to a positive reference standard and a negative reference standard, wherein a statistical similarity of the level of at least one or more anti-endothelial cell antibodies to the positive reference standard indicates an increased likelihood of developing an allograft rejection and a statistical similarity of the level of at least one or more anti-endothelial cell antibodies to the negative reference standard indicates a decreased likelihood of developing an allograft rejection.

In some embodiments described herein is a solid-phase immunoassay for detecting at least one or more anti-endothelial cell antibodies. In some aspects, the steps of performing the solid-phase immunoassay comprises: isolating at least one or more anti-endothelial cell antibodies with a capture element or antibody isolation method described herein and measuring the level of at least one or more anti-endothelial cell antibodies specific to at least a portion or peptide fragment at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 of the proteins listed in Table 2. In some aspects, the levels of these anti-endothelial cell antibodies are then compared to a positive reference standard and a negative reference standard, wherein a statistical similarity of the level of at least one or more anti-endothelial cell antibodies to the positive reference standard indicates an increased likelihood of developing an allograft rejection and a statistical similarity of the level of at least one or more anti-endothelial cell antibodies to the negative reference standard indicates a decreased likelihood of developing an allograft rejection.

In some embodiments described herein is a solid-phase immunoassay for detecting an anti-endothelial cell antibody. In some aspects, the steps of performing the solid-phase immunoassay comprises: isolating at least one or more anti-endothelial cell antibodies with a capture element or antibody isolation method described herein; measuring the level of at least one or more anti-endothelial cell antibodies specific to at least a portion or peptide fragment of endoglin, Fms-like tyrosine kinase-3 (FLT3) ligand, EGF-like repeats and discoidin I-like domains 3 (EDIL3) and intercellular adhesion molecule 4 (ICAM4). In some aspects, the levels of Fms-like tyrosine kinase-3 (FLT3) ligand, EGF-like repeats and discoidin I-like domains 3 (EDIL3) and intercellular adhesion molecule 4 (ICAM4) are compared to a positive reference standard and a negative reference standard, wherein a statistical similarity of the level of at least one or more anti-endothelial cell antibodies to the positive reference standard indicates an increased likelihood of developing an allograft rejection and a statistical similarity of the level of at least one or more anti-endothelial cell antibodies to the negative reference standard indicates a decreased likelihood of developing an allograft rejection.

In some aspects, the anti-endothelial cell antibody target antigen is expressed on the cell surface of an endothelial cell. In some aspects the anti-endothelial cell antibody target antigens is not expressed on the cell surface of an endothelial cell. In some aspects, the anti-endothelial cell antibody target antigen is expressed on and endothelial cell at the beginning stages of transplant rejection and decreases in expression during the rejection process. In some aspects, the anti-endothelial cell antibody target antigen is expressed on and endothelial cell at the beginning stages of transplant rejection and retains its expression throughout the rejection process. In some aspects, the anti-endothelial cell antibody antigen is stained by immunohistochemical methods known in the art from tissue biopsies taken before or after an organ transplant.

In some embodiments described herein, the presence of one or more HLA antibodies may be detected using a solid phase immuno assay (e.g., a sandwich ELISA type assay), see, for example, U.S. Pat. No. 6,046,013, which is incorporated by reference herein for its teachings thereof. In some embodiments assays described herein for detecting specific anti-endothelial cell antibodies are carried out at the same time as an assay for detecting the presence of HLA antibodies. In some embodiments the two assays are carried out at different times for determining whether a recipient has both anti-endothelial cell antibodies and HLA antibodies. In some aspects, recipients having both anti-endothelial cell antibodies and HLA antibodies are more likely to have an allograft rejection.

In some embodiments, an ELISA sandwich type assay is used for HLA-typing, similar to conventional immunoassays for cross-match testing. A sandwich assay is performed by first attaching a capture agent specific for the HLA to a solid support. The capture agent may be bound to the surface by any convenient means, depending upon the nature of the surface. Where the capture agent is antibody, it may be bound to the plates covalently or non-covalently.

In some embodiments, the isolated anti-endothelial cell antibodies are detected by a specific labeled detection reagent and the intensity of the label is measured for determining allograft rejection. In some embodiments, the isolated HLA antibodies are detected by a specific labeled detection reagent and the intensity of the label is measured. In some embodiments, the labeled reagent is a class specific (e.g., IgG, IgA, IgM, IgE, IgD) anti-human antibody, e.g. antisera. In some embodiments, anti-human antibodies are labeled with a covalently bound enzyme capable of providing a detectable signal after addition of a suitable substrate. One enzyme, alkaline phosphatase, reacts with PNPP (p-nitrophenyl phosphate), a substrate used with alkaline phosphatase to produce a measurable color under appropriate reaction conditions. The color intensity, using a constant reaction time, is proportional to the amount of enzyme attached to the well which is further indicative of the amount of background captured to each well. Light absorbance between about 400 to 420 nm is measured with a spectrophotometer. The color measurement that develops in each well with each normal (non-immunized) serum is recorded and an average is obtained for replicative wells. Examples of other suitable enzymes for use in conjugates include horseradish peroxidase, alkaline phosphatase, malate dehydrogenase and the like. Other non-limiting examples of labels which permit direct measurement of antibodies include radiolabels, fluorophores, dyes, beads, chemiluminescers, colloidal particles, and the like. Appropriate substrates for other enzyme conjugates and suitable reaction conditions are known to those skilled in the art.

In some embodiments, a positive reference standard is any positive serum or sera, which has been previously shown to have anti-endothelial cell antibodies in an endothelial cross-match test. In some aspects, the positive sera are from a patient sample or samples that have also been shown to have had an allograft rejection. In some aspects, the positive sera are from a patient sample or samples that were sensitized or reactive to HLA. In some aspects, the positive reference standard has also been shown to be have anti-endothelial cell antibodies to at least a portion or peptide fragment of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 of the proteins listed in Table 2. In some aspects, the positive reference standard has been shown to have anti-endothelial cell antibodies to at least a portion or peptide fragment of endoglin, Fms-like tyrosine kinase-3 (FLT3) ligand, EGF-like repeats and discoidin I-like domains 3 (EDIL3) and intercellular adhesion molecule 4 (ICAM4).

In some embodiments, a negative reference standard is any negative serum or sera, which has been previously shown to have anti-endothelial cell antibodies in an endothelial cross-match test. In some aspects, the negative sera are from a patient sample or samples that have also been shown to not have had an allograft rejection. In some aspects, the negative sera are from a patient sample or samples that were not sensitized or reactive to HLA. In some aspects, the negative reference standard has also been shown to not have anti-endothelial cell antibodies to at least a portion or peptide fragment of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 of the proteins listed in Table 2. In some aspects, the negative reference standard has been shown to not have anti-endothelial cell antibodies to at least a portion or peptide fragment of endoglin, Fms-like tyrosine kinase-3 (FLT3) ligand, EGF-like repeats and discoidin I-like domains 3 (EDIL3) and intercellular adhesion molecule 4 (ICAM4).

In some embodiments, the positive reference standard further comprises an HLA antibody positive serum or sera, which has previously been shown to have HLA antibodies (e.g., by a cross-match test). In some embodiments, the negative reference standard further comprises an HLA negative serum or sera, which has previously been shown to not have HLA antibodies (e.g., by cross-match test). In some aspects, the HLA positive and negative sera are useful for determining if a subject has HLA antibodies in addition to anti-endothelial cell antibodies.

In some embodiments, the positive and negative reference standards described herein are used to provide a threshold or cut off value for the presence of an anti-endothelial cell antibody establishing whether an individual has an AR or predict whether an individual will incur an AR. The exact level of the threshold is immaterial because the determined expression values are relative to a positive or negative reference standard and are dependent upon the detecting instrument being used, reagent concentration, operator, and sample qualities.

In some embodiments, a reference standard curve may be used to quantitate the levels or concentration of an anti-endothelial cell antibody. The reference standard curve may be used to determine a relative detection unit, for example, a relative fluoresence unit (RFU) used in solid phase immunoassays. As described herein, a reference standard curve for one or more anti-endothelial cell antibodies may be generated by taking a known amount of an anti-endothelial cell antibody and quantitating the relative detection unit per micro gram of protein across a range of concentrations of the anti-endothelial cell antibody being measured. In one aspect described herein, a reference standard curve may be utilized to determine an amount of an anti-endothelial cell antibody in a positive reference standard. In another aspect described herein, a reference standard curve may be utilized to determine an amount of an anti-endothelial cell antibody in a negative reference standard. In another aspect described herein, a reference standard curve may be utilized to determine an amount of an anti-endothelial cell antibody in an unknown or test sample (e.g., a sample obtained from a subject to determine the subject is undergoing an allograft rejection).

Methods of Diagnosing or Predicting an Allograft Rejection with Anti-Endothelial Cell Antibodies In one embodiment described herein, is a method of predicting the likelihood of an allograft rejection. In one aspect the method comprises detecting at least one or more anti-endothelial cell antibodies with a capture element or antibody isolation method described herein; measuring the level of at least one or more anti-endothelial cell antibodies specific to at least a portion or peptide fragment of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 proteins listed in Table 2. In some aspects, the levels of these anti-endothelial cell antibodies are then compared to a positive reference standard and a negative reference standard, wherein a statistical similarity of the level of at least one or more anti-endothelial cell antibodies to the positive reference standard indicates an increased likelihood of developing an allograft rejection and a statistical similarity of the level of at least one or more anti-endothelial cell antibodies to the negative reference standard indicates a decreased likelihood of developing an allograft rejection.

In one embodiment described herein, is a method of predicting the likelihood of an allograft rejection. In one aspect the method comprises detecting at least one or more anti-endothelial cell antibodies with a capture element or antibody isolation method described herein; measuring the level of at least one or more anti-endothelial cell antibodies specific to at least a portion or peptide fragment of endoglin, Fms-like tyrosine kinase-3 (FLT3) ligand, EGF-like repeats and discoidin I-like domains 3 (EDIL3) and intercellular adhesion molecule 4 (ICAM4). In some aspects, the levels of the anti-endothelial cell antibodies to Fms-like tyrosine kinase-3 (FLT3) ligand, EGF-like repeats and discoidin I-like domains 3 (EDIL3) and intercellular adhesion molecule 4 (ICAM4) are then compared to a positive reference standard and a negative reference standard, wherein a statistical similarity of the level of at least one or more anti-endothelial cell antibodies to the positive reference standard indicates an increased likelihood of developing an allograft rejection and a statistical similarity of the level of at least one or more anti-endothelial cell antibodies to the negative reference standard indicates a decreased likelihood of developing an allograft rejection.

In some embodiments described herein, is a method of predicting the likelihood of an allograft rejection. In one aspect, the method comprises measuring the level of at least one or more anti-endothelial cell antibodies specific to at least a portion or peptide fragment of endoglin, Fms-like tyrosine kinase-3 (FLT3) ligand, EGF-like repeats and discoidin I-like domains 3 (EDIL3) and intercellular adhesion molecule 4 (ICAM4). In another aspect, the method further comprises measuring the level of at least one or more HLA class I and class II antibodies. In some aspects, the levels of Fms-like tyrosine kinase-3 (FLT3) ligand, EGF-like repeats and discoidin I-like domains 3 (EDIL3), intercellular adhesion molecule 4 (ICAM4), and HLA class I and HLA class II antibodies are then compared to a positive reference standard and a negative reference standard, wherein a statistical similarity of the level of at least one or more anti-endothelial cell antibodies to the positive reference standard indicates an increased likelihood of developing an allograft rejection and a statistical similarity of the level of at least one or more anti-endothelial cell antibodies to the negative reference standard indicates a decreased likelihood of developing an allograft rejection.

In some embodiments described herein, the method of predicting the likelihood of an allograft rejection may further comprise testing the activation state of a pre-established culture of endothelial cells as described herein by contacting the endothelial cells with a sample from a subject. In some aspects, the sample is an elution or isolation of antibodies following a cross match test as described herein. In some aspects, one or more markers selected from Table 4 may be measured to determine an endothelial cell activation signature, which indicates an increased likelihood for an allograft rejection event. In another aspect, the endothelial activation signature may comprise the increased or decreased expression of any one or more of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, or at least 54 of the inflammatory cytokines listed in Table 4. In another aspect, the endothelial activation signature may comprise the increased or decreased expression of any one or more of HLA class I gene. E selectin, PECAM1, or ICAM1. In another aspect, the endothelial cell activation signature includes increased levels of the PDGF, RANTES (i.e., CCL5), and RESISTIN. In another aspect, the endothelial cell activation signature includes the decreased level of CCL3, CCL4, CXCL5, and CXCL.

In one embodiment described herein, is a method of treating a patient suspected of having an allograft rejection. In one aspect the method comprises ordering a clinical test comprising detecting at least one or more anti-endothelial cell antibodies with a capture element or antibody isolation method described herein; measuring the level of at least one or more anti-endothelial cell antibodies specific to at least a portion or peptide fragment of comprising endoglin, Fms-like tyrosine kinase-3 (FLT3) ligand, EGF-like repeats and discoidin I-like domains 3 (EDIL3) and intercellular adhesion molecule 4 (ICAM4). In some aspects, the levels of anti-endothelial cell antibodies to Fms-like tyrosine kinase-3 (FLT3) ligand, EGF-like repeats and discoidin I-like domains 3 (EDIL3) and intercellular adhesion molecule 4 (ICAM4) are then compared to a positive reference standard and a negative reference standard, wherein a statistical similarity of the level of at least one or more anti-endothelial cell antibodies to the positive reference standard indicates an increased likelihood of developing an allograft rejection and a statistical similarity of the level of at least one or more anti-endothelial cell antibodies to the negative reference standard indicates a decreased likelihood of developing an allograft rejection. In some aspects, the therapeutic regimen is increased if the patient is indicated as having an increased likelihood of developing an allograft rejection or decreased if the patient is indicated as having a decreased likelihood of developing an allograft rejection.

In one embodiment described herein, is a method of treating a patient suspected of having an acute rejection. In one aspect, the method comprises ordering a clinical test comprising measuring the level of at least one or more anti-endothelial cell antibodies specific to at least a portion or peptide fragment of endoglin, Fms-like tyrosine kinase-3 (FLT3) ligand, EGF-like repeats and discoidin I-like domains 3 (EDIL3) and intercellular adhesion molecule 4 (ICAM4). In another aspect, the method further comprises measuring the level of at least one or more HLA class I and class II antibodies. In some aspects, the levels of anti-endothelial cell antibodies to Fms-like tyrosine kinase-3 (FLT3) ligand, EGF-like repeats and discoidin I-like domains 3 (EDIL3), intercellular adhesion molecule 4 (ICAM4), and HLA class I and HLA class II antibodies are then compared to a positive reference standard and a negative reference standard, wherein a statistical similarity of the level of at least one or more anti-endothelial cell antibodies to the positive reference standard indicates an increased likelihood of developing an allograft rejection and a statistical similarity of the level of at least one or more anti-endothelial cell antibodies to the negative reference standard indicates a decreased likelihood of developing an allograft rejection. In some aspects, the therapeutic regimen is increased if the patient is indicated as having an increased likelihood of developing an allograft rejection or decreased if the patient is indicated as having a decreased likelihood of developing an allograft rejection.

The detection of the presence or absence of anti-endothelial cell antibodies in addition to the detection of the presence or absence HLA antibodies can also be used to identify an individual for treatment of AR. In some embodiments, this individual is monitored for the progression or regression of AR symptoms. In some embodiments, this individual is treated for AR prior to or at the onset of AR symptoms. In some embodiments, the treatment is corticosteroid therapy. In other embodiments, the treatment is administration of an anti-T-cell antibody, such as muromonab-CD3 (Orthoclone OKT3). In further embodiments, the treatment is a combination of plasma exchange and administration of anti-CD20 antibodies. In some cases, the monitoring is done to determine if the treatment should be continued or to see if the treatment is efficacious.

In some embodiments of the methods described herein, the methods have use in predicting AR response. In these methods, a subject is first monitored for AR according to the subject methods, and then treated using a protocol determined, at least in part, on the results of the monitoring. In one embodiment, the subject is monitored for the presence or absence of acute rejection according to one of the methods described herein. The subject may then be treated using a protocol whose suitability is determined using the results of the monitoring step. For example, where the subject is predicted to have an acute rejection response within the next 1 to 6 months, immunosuppressive therapy can be modulated, e.g., increased or drugs changed, as is known in the art for the treatment/prevention of acute rejection. Likewise, where the subject is predicted to be free of current and near-term acute rejection, the immunosuppressive therapy can be reduced in order to reduce the potential for drug toxicity. In some embodiments of the methods described herein, a subject is monitored for acute rejection following receipt of a graft or transplant. The subject may be screened once or serially following transplant receipt, e.g., weekly, monthly, bimonthly, half-yearly, yearly, etc. In some embodiments, the subject is monitored prior to the occurrence of an acute rejection episode. In other embodiments, the subject is monitored following the occurrence of an acute rejection episode.

In some embodiments of the methods described herein, the methods have use in altering or changing a treatment paradigm or therapeutic regimen of a subject in need of treatment of AR. Exemplary non-limiting immunosuppressive therapeutics or therapeutic agents useful for the treating of a subject in need thereof comprise steroids (e.g., prednisone (Deltasone), prednisolone, methyl-prednisolone (Medrol, Solumedrol)), antibodies (e.g., muromonab-CD3 (Orthoclone-OKT3), antithymocyte immune globulin (ATGAM, Thymoglobulin), daclizumab (Zenapax), basiliximab (Simulect), Rituximab, cytomegalovirus-immune globulin (Cytogam), immune globulin (Polygam)), calcineurin inhibitors (e.g., cyclosporine (Sandimmune), tacrolimus (Prograf)), antiproliferatives (e.g., mycophenolate mofetil (Cellcept), azathioprine (Imuran)), TOR inhibitors (e.g., rapamycin (Rapamune, sirolimus), everolimus (Certican)), therapeutic plasmapheresis or a combination therapy thereof.

In some embodiments, wherein a subject is identified as not having an AR using the methods described herein, the subject can remain on an immunosuppressive standard of care maintenance therapy comprising the administration of an antiproliferative agent (e.g., mycophenolate mofetil and/or azathioprine), a calcineurin inhibitor (e.g., cyclosporine and/or tacrolimus), steroids (e.g., prednisone, prednisolone, and/or methyl prednisolone) or a combination thereof. For example, a subject identified as not having an AR using the methods described herein can be placed on a maintenance therapy comprising the administration of a low dose of prednisone (e.g., about 0.1 $mg \cdot kg^{-1} \cdot d^{-1}$ to about 1 $mg \cdot kg^{-1} \cdot d^{-1}$), a low dose of cyclosporine (e.g., about 4 $mg \cdot kg^{-1} \cdot d^{-1}$ to about 8 $mg \cdot kg^{-1} \cdot d^{-1}$), and a low dose of mycophenolate (e.g., about 1-1.5 g twice daily). In another example, a subject identified as not having an AR using the methods described herein can be taken off of steroid therapy and placed on a maintenance therapy comprising the administration of a low dose of cyclosporine (e.g., about 4 $mg \cdot kg^{-1} \cdot d^{-1}$ to about 8 $mg \cdot kg^{-1} \cdot d^{-1}$), and a low dose of mycophenolate (e.g., about 1-1.5 g twice daily). In another example, a subject identified as not having an AR using the methods described herein can be removed from all immunosuppressive therapeutics described herein.

In some embodiments, wherein a subject is identified as having an AR using the methods described herein, the subject may be placed on a rescue therapy or increase in immunosuppressive agents comprising the administration of a high dose of a steroid (e.g., prednisone, prednisolone, and/or methyl prednisolone), a high dose of a polyclonal or monoclonal antibody (e.g., muromonab-CD3 (OKT3), anti-thymocyte immune globulin, daclizumab, Rituximab, basiliximab, cytomegalovirus-immune globulin, and/or immune globulin), a high dose of an antiproliferative agent (e.g., mycophenolate mofetil and/or azathioprine), or a combination thereof.

In some embodiments, the course of therapy wherein a subject is identified as not having an AR or is identified as having an AR using the methods described herein is dependent upon the time after transplantation and the severity of rejection, treating physician, and the transplantation center.

Therefore, detecting the presence or absence anti-endothelial cell antibodies in addition to detecting of the presence or absence of HLA antibodies using the methodology described herein allows for the diagnosis of AR in a allograft recipient, diagnosis of no-AR in a allograft recipient, aid in the diagnosis of AR, aid in the diagnosis of the risk of AR, monitor the progression of AR, monitor the regression of AR, identify an individual who should be treated for AR or continue to be treated for AR, assess efficacy of treatment for AR, and/or identify individuals who should be monitored for AR symptoms.

In some embodiments, the detection of the presence or absence anti-endothelial cell antibodies in addition to the detection of the presence or absence HLA antibodies by the methodology described herein can be used for the stratification or identification of antibody mediated AR. In some embodiments, the detection of the presence or absence anti-endothelial cell antibodies in addition to the detection of the presence or absence HLA antibodies by the methodology described herein can be used for the stratification or identification of T-cell mediated AR. The detection of the presence or absence of anti-endothelial cell antibodies in addition to the detection of the presence or absence of HLA antibodies by the methodology described herein is useful for identification of B-cell or T-cell mediated AR in some aspects because they are either expressed on B cells or are expressed on T-cells or are known markers of activated T-cells.

Kits for the Diagnosis, Detection, or Prediction of AR

In some embodiments described herein are assay kits for the diagnosis, detection, and prediction of AR. In some embodiments the kit comprises a solid-phase immunoassay (e.g., an ELISA) for the capturing and measuring anti-endothelial cell antibodies in a biological sample. In some aspects, the kit further includes positive and negative reference standards for determining whether a biological sample has anti-endothelial cell antibodies. In some aspects, the kit is useful for diagnosing or predicting the likelihood that an individual has or will have an AR.

In some embodiments, the kit comprises an antibody detection element for measuring the level of an anti-endothelial cell antibody present in a biological sample from an individual that has received or will receive an organ transplant. In some embodiments, the kit comprises an antibody capture element comprising a full length protein, protein fragment, peptide, polypeptide, recombinant peptide, recombinant protein, or a polypeptide fragment corresponding to at least a portion or peptide fragment of at least one protein listed in Table 2. In some embodiments, the kit comprises an antibody capture element comprising a full length protein, protein fragment, peptide, polypeptide, recombinant peptide, recombinant protein, or a polypeptide fragment corresponding to at least a portion or peptide fragment of endoglin, Fms-like tyrosine kinase-3 (FLT3) ligand, EGF-like repeats and discoidin I-like domains 3 (EDIL3) and intercellular adhesion molecule 4 (ICAM4). In some embodiments, the kit comprises a solid substrate comprising a bead, plate, or microtiter plate. In some aspects, the kit comprises a microtiter plate coated with streptavidin. In some aspects, the kit comprises a detection reagent. In some aspects, the detection reagent is a labeled class specific (e.g., IgG, IgA, IgM, IgE, IgD) anti-human secondary antibody.

In some embodiments, the kit further comprises a solid substrate comprising a bead, plate, or microtiter plate, wherein a full length protein, protein fragment, peptide, polypeptide, recombinant peptide, recombinant protein, or a polypeptide fragment corresponding to at least a portion or peptide fragment of at least one protein listed in Table 2 is linked. In some aspects, the kit further comprises a solid substrate comprising a bead, plate, or microtiter plate, wherein a full length protein, protein fragment, peptide, polypeptide, recombinant peptide, recombinant protein, or a polypeptide fragment corresponding to at least a portion or peptide fragment of endoglin, Fms-like tyrosine kinase-3 (FLT3) ligand, EGF-like repeats and discoidin I-like domains 3 (EDIL3) and intercellular adhesion molecule 4 (ICAM4) is linked.

In some embodiments, the kit further comprises a positive reference standard and a negative reference standard for comparing assay results and determining whether an individual has an AR or will have an AR as described herein. In some aspects, the positive reference standard is a positive serum or sera, which has been previously shown to have anti-endothelial cell antibodies in an endothelial cross-match test. In some aspects, the positive reference standard is a positive serum or sera, which has been previously shown to have anti-endothelial cell antibodies specific to at least a portion or peptide fragment of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 proteins listed in Table 2. In some aspects, the negative reference standard is a negative serum or sera, which has been previously shown to not have anti-endothelial cell antibodies in an endothelial cross-match test. In some aspects, the negative reference standard is a negative serum or sera, which has been previously shown to not have anti-endothelial cell antibodies specific to at least a portion or peptide fragment of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 proteins listed in Table 2.

In some embodiments, the comparison is performed by a computer program. In some embodiments, the comparison is performed by an individual. In some embodiments, the comparison is performed by a physician. In some embodiments, the comparison is useful for diagnosing and individual as having an AR or having an increased likelihood of incurring an AR.

In some embodiments, the kits comprise a computer program. In some embodiments a computer program is configured to output to a user a score representing an increased or decreased likelihood of at least one of: a prediction of an onset of an AR response, a diagnosis of an AR response, and a characterization of an AR response in the subject, wherein the output is determined by comparing levels of anti-endothelial cell antibodies in a test sample (e.g., from an allograft recipient) to a negative reference standard and a positive reference standards described herein.

The kit also comprises instructions for the use of the assay.

It will be readily apparent to one of ordinary skill in the relevant arts that suitable modifications and adaptations to the compositions, methods, kits, and applications described herein can be made without departing from the scope of any embodiments or aspects thereof. The compositions and methods provided are exemplary and are not intended to limit the scope of the claimed embodiments. All of the various embodiments, aspects, and options disclosed herein can be combined in all variations. The scope of the compositions and methods described herein include all actual or potential combinations of embodiments, aspects, options, examples, and preferences herein described.

EXAMPLES

Figure 1:
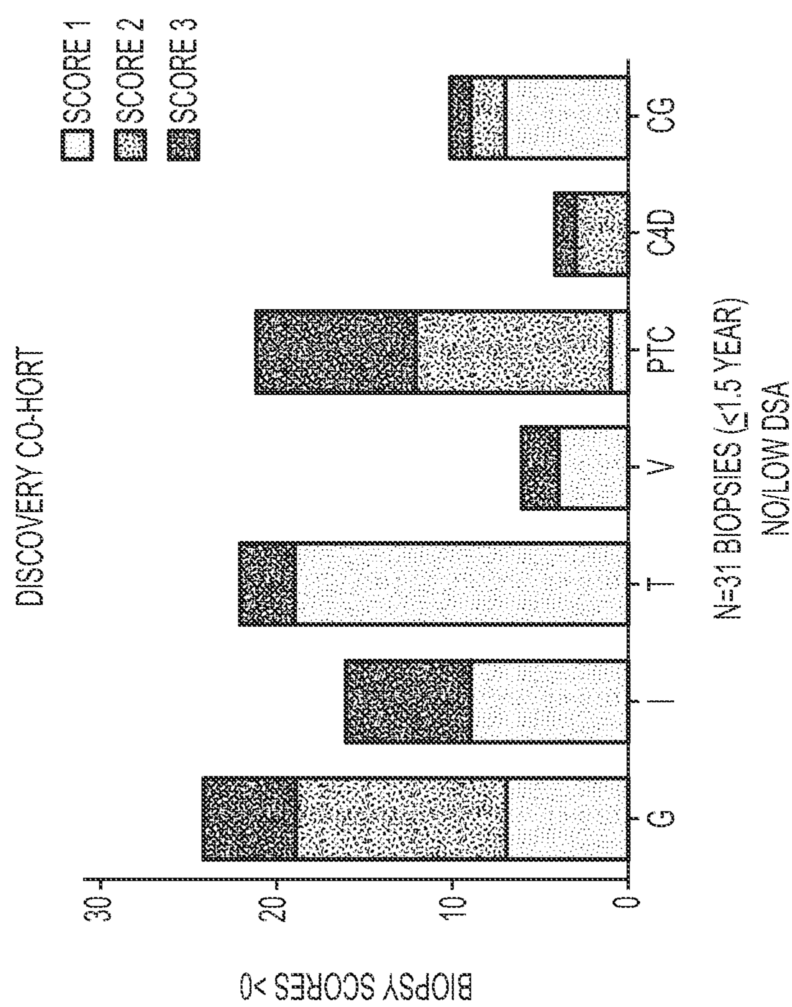
FIG. 1 Histopathology Scores for Discovery Cohort Transplant Recipients.

Example 1: Identification of Novel Antigenic Endothelial Cell Targets Using Protein Arrays AECAs were isolated from a Discovery Cohort of ten renal transplant recipients whose demographics are provided in Table 1. The majority (9 of 10) was sensitized to HLA and all tested positive for AECAs in pre-transplant endothelial cell crossmatch tests. Nine experienced allograft dysfunction and biopsy proven rejection with noted glomerulitis and peritubular capillaritis (FIG. 1). Only one recipient had antibody to donor-HLA (DR52) at the time of rejection. To focus our analyses on AECA target antigens, antibody eluates were generated using ECPs derived from blood. In brief, each serum was incubated with ECPs and, following wash steps, the bound antibodies were acid eluted and neutralized. Using a high-density protein platform, we profiled AECA eluates from the ten Discovery Cohort recipients against approximately 9500 human proteins. Four proteins, expressed on vascular endothelium, endoglin, EDIL3, ICAM4 and FLT3 ligand, were identified in all eluates. Signal intensities for these four antibodies were significant (endoglin, EDIL3, and FLT3 $p<0.001$; ICAM4 $p<0.03$) when compared to low abundance antibodies with signals<2000 RFU FIG. 2A and Table 2. We also performed analyses of AECA elutes derived from two recipients undergoing therapeutic plasmapheresis for rejection. These AECA eluates were derived from endothelial cell crossmatch positive sera drawn prior to transplantation, crossmatch negative sera obtained at the end of treatment, and sera drawn later post-treatment (3 and 9 months) that again tested positive in an endothelial cell crossmatch. Protein array data, normalized to total IgG immunoglobulin, showed that AECAs for all four protein targets (endoglin, FLT3 ligand, EDIL3 and ICAM4) decreased following plasmapheresis and rebounded again in sera that had AECAs detectable in crossmatch tests FIG. 2B.

TABLE 1

Demographics of Renal Transplant Patients

| Demographics | Discovery Cohort N = 10 | ELISA Test Cohort N = 150 |
|---|---|---|
| Recipient Age (mean, SD) | 58 ± 9 | 49 ± 15 |
| Race (% non-white) | 10% | 44% |
| Male Gender (%) | 90% | 41% |
| Previous transplantation (%) | 60% | 40% |
| HLA Sensitization[1] (%) | 90% | 91% |
| Mean % CPRA[2] (CDC-XM, FCXM) | 18, 38 | 29, 39 |
| Original ABO or HLA barrier[3]: (%) | | |
| ABOi | 20% | 6% |
| CDC-XM+ | 0 | 2% |
| FCXM+ | 10% | 19% |
| FCXM−, DSA+ | 40% | 45% |
| NO DSA | 50% | 34% |
| Donor (Mean Age) | 45 ± 12 | 40 ± 15 |
| Live Donor (%) | 70% | 55% |
| Deceased Donor (%) | 30% | 45% |
| HLA-A; B; DR; DQ mismatch (mean) | 5.0 | 4.7 |
| Plasmapheresis Treatments: | | |
| No Pre- or Post-Treatments (%) | 20% | 45% |
| Pre-transplant (Mean, Median) | 2.5, 1.5 | 1.0, 0.0 |
| Post-transplant (Mean, Median) | 4.4, 3.5 | 4.0, 2.0 |
| anti-CD25 induction (%) | 40% | 17% |
| Thymoglobulin induction (%) | 60% | 83% |
| Rituximab induction (%) | 30% | 36% |

[1]HLA-specific antibody detected on Luminex ® platforms

[2]Calculated panel reactive antibody (CPRA) was determined for HLA-antibodies of sufficient strength to yield a positive CDC crossmatch (CDC-XM) or flow cytometric crossmatch (FCXM)

[3]Original donor HLA-specific antibody (DSA) strength prior to desensitization treatments

Example 2 Novel Antigenic Targets of Anti-Endothelial Cell Antibodies

Anti-endothelial cell antibody target antigens identified from antibody eluates from ECPs in human protein arrays are listed in Table 2 below. Each anti-endothelial cell antibody formed an antibody/antigen complex and was identified at a threshold cut off RFU >2,000.

TABLE 2

Anti-endothelial cell antibody target proteins (antigens)

| Protein Name (corresponding to array peptide/antigen) | Gene Symbol | Gene ID | Average RFU |
|---|---|---|---|
| Recombinant human CTLA-4/Fc | CTLA4 | 1493 | 58077.0 |
| tripartite motif-containing 21 (TRIM21) | TRIM21 | 6737 | 39835.7 |
| hematopoietic SH2 domain containing (HSH2D) | HSH2D | 84941 | 28572.5 |
| interferon, alpha-inducible protein 6 (IFI6) | IFI6 | 2537 | 15892.2 |
| APEX nuclease (apurinic/apyrimidinic endonuclease) 2 (APEX2), nuclear gene encoding mitochondrial protein | APEX2 | 27301 | 12493.3 |

TABLE 2-continued

Anti-endothelial cell antibody target proteins (antigens)

| Protein Name (corresponding to array peptide/antigen) | Gene Symbol | Gene ID | Average RFU |
|---|---|---|---|
| CAP-GLY domain containing linker protein family, member 4 (CLIP4) | CLIP4 | 79745 | 10955.7 |
| UBX domain containing 8 (UBXD8/FAF2) | UBXD8 | 23197 | 8636.5 |
| zinc finger, MYM-type 5 (ZMYM5) | ZMYM5 | 9205 | 8260.8 |
| EGF-like repeats and discoidin I-like domains 3 (EDIL3) | EDIL3 | 10085 | 8232.8 |
| ubiquitin-conjugating enzyme E2 variant 1 (UBE2V1) | UBE2V1 | 7335 | 7955.9 |
| phosphoglycerate dehydrogenase (PHGDH) | PHGDH | 26227 | 7405.2 |
| sciellin (SCEL) | SCEL | 8796 | 7255.3 |
| Zinc finger CCHC domain-containing protein 8 | ZCCHC8 | 55596 | 5908.2 |
| chromosome 22 open reading frame 33 (C22orf33/Tex33) | C22orf33 | 339669 | 5578.2 |
| cleavage and polyadenylation specific factor 3, 73 kDa (CPSF3) | CPSF3 | 51692 | 5425.6 |
| Uncharacterized protein C20orf96 | C20orf96 | 140680 | 5031.8 |
| endoglin (Osler-Rendu-Weber syndrome 1) (ENG) | ENG | 2022 | 4966.8 |
| Disks large homolog 3 | DLG3 | 1741 | 4352.0 |
| cyclin G associated kinase (GAK) | GAK | 2580 | 4298.4 |
| CDC42 effector protein (Rho GTPase binding) 3 (CDC42EP3) | CDC42EP3 | 10602 | 4280.3 |
| ADP-ribosylation factor FTPase activating protein 1 (ARFGAP1), transcript variant 2 | ARFGAP1 | 55738 | 4211.4 |
| baculoviral IAP repeat-containing 4 (BIRC4) | XIAP | 331 | 4108.5 |
| chromosome 2 open reading frame 47 (C2orf47) | C2orf47 | 79568 | 3597.3 |
| quaking homolog, KH domain RNA binding (mouse) (QKI), transcript variant 4 | QKI | 9444 | 3493.8 |
| intercellular adhesion molecule 4 (Landsteiner-Wiener blood group) (ICAM4), transcript variant 1 | ICAM4 | 3386 | 3412.4 |
| fms-related tyrosine kinase 3 ligand (FLT3LG) | FLT3LG | 2323 | 3383.8 |
| hypothetical protein LOC51233, mRNA (cDNA clone MGC: 75009 IMAGE: 5170001), complete cds. | DRICH1 | 51233 | 3331.7 |
| Parkinson disease 7 domain containing 1 (PDDC1) | PDDC1 | 347862 | 3296.6 |
| forkhead box P1 (FOXP1) | FOXP1 | 27086 | 3267.5 |
| nudix (nucleoside diphosphate linked moiety X)-type motif 16-like 1 (NUDT16L1) | NUDT16L1 | 84309 | 3256.8 |
| ubiquilin 2 (UBQLN2) | UBQLN2 | 29978 | 3129.8 |
| TOX high mobility group box family member 2 (TOX2), transcript variant 3 | TOX2 | 84969 | 3102.1 |
| AF4/FMR2 family, member 4 (AFF4) | AFF4 | 27125 | 3050.3 |
| CWF19-like 2, cell cycle control (*S. pombe*) (CWF19L2) | CWF19L2 | 143884 | 2924.5 |
| glutaryl-Coenzyme A dehydrogenase (GCDH), nuclear fene encoding mitochondrial protein, transcript variant 1 | GCDH | 2639 | 2666.8 |
| Protein FAM184A (C6orf60) | FAM184A | 79632 | 2661.1 |
| SMT3 suppressor of mif two 3 homolog 1 (*S. Cerevisiae*) (SUMO1), transcript variant 1 | SUMO1 | 474338 | 2559.8 |
| Chromogranin B (secretogranin 1) (CHGB) | CHGB | 1114 | 2559.3 |
| zinc finger protein 695 (ZNF695) | ZNF695 | 57116 | 2529.8 |
| LIM homeobox transcription factor 1, alpha (LMX1A) | LMX1A | 4009 | 2476.6 |
| complexin 2 (CPLX2), transcript variant 2 | CPLX2 | 10814 | 2435.8 |
| myotilin (MYOT) | MYOT | 9499 | 2362.6 |
| sorting nexin 13 (SNX13) | SNX13 | 23161 | 2324.0 |
| intercellular adhesion molecule 4 (Landsteiner-Wiener blood group) (ICAM4) | ICAM4 | 3386 | 2268.7 |
| centrosome and spindle pole associated protein 1 (CSPP1), transcript variant 2 | CSPP1 | 79848 | 2256.9 |
| glycogenin 2 (GYG2) | GYG2 | 8908 | 2227.8 |
| outer dense fiber of sperm tails 2 (ODF2) | ODF2 | 4957 | 2226.6 |
| transcriptional adaptor 3 (NGG1 homolog, yeast)-like (TADA3L), transcript variant 2 | TADA3 | 10474 | 2204.3 |
| aquaporin 2 (collecting duct) (AQP2) | AQP2 | 359 | 2197.4 |
| dystrophin (muscular dystrophy, Duchenne and becker types) (DMD), transcript variant Dp71b | DMD | 1756 | 2136.8 |
| hypothetical protein FLJ22795 (FLJ22795) | GOLGA2P10 | 80154 | 2117.2 |
| muted homolog (mouse) (MUTED) | MUTED | 63915 | 2096.1 |
| proline/arginine-rich end leucine-rich repeat protein (PRELP), transcript variant 1 | PRELP | 5549 | 2063.3 |
| major histocompatibility complex, class II, DP alpha 1 (HLA-DPA1) | HLA-DPA1 | 3113 | 2053.5 |
| testis-specific serine kinase 2 (TSSK2) | TSSK2 | 23617 | 2046.3 |

Example 3: Expression of Target Antigens on Endothelial Cells

Cell phenotype analysis using flow cytometry confirmed surface expression of endoglin, EDIL3, ICAM4 and FLT3 (receptor for FLT3 ligand) on blood derived ECPs when compared to an isotype control antibody (data not shown). Analysis of two EC lines, derived from iliac artery and human umbilical vein, yielded positive staining for endoglin, but negative staining for EDIL3, ICAM4, and FLT3, even following TNFα stimulation. To investigate expression of these antigenic targets in renal tissue, immunohistochemistry was performed on rejection biopsies obtained from the ten Discovery Cohort recipients. FIG. 3 illustrates representative staining for endoglin and FLT3, which were expressed on arterial endothelium and glomerular and peritubular capillaries. Concomitant staining of biopsy tissue for FLT3LG, EDIL3 and ICAM4 yielded negative results.

Example 4: Incidence of AECAs Using Antigen Specific ELISAs

Sera from 150 sequential renal transplant recipients, for whom there were adequate pre- and post-transplant (≤3 months) sera, were tested using MSD ELISAs specific for endoglin, EDIL3, ICAM4 and FLT3. This retrospective study cohort was similar to the Discovery Cohort in that it was enriched for recipients sensitized to HLA, with 91% (137 of 150) testing positive for HLA-specific class I and/or class II antibodies Table 1.

We analyzed the most strongly reacting sera in each ELISA, in which the signal intensity was equal to or greater than the trimmed mean. Fifty-six sera (37%) reacted positively with one or more antigenic targets. Within this group, 36 sera (24%) showed strong reactivity with all four antigen targets Table 3. Pairwise comparisons performed using the top 36 reacting sera yielded highly significant (P<0.0005) correlations in antibody production for these four antigens: endoglin and EDIL3 (R2=0.91, r=0.954), endoglin and ICAM4 (R2=0.89, r=0.94), and EDIL3 and ICAM4 (R2=0.87, r=0.93), FLT3 and endoglin (R2=0.74, r=0.86), FLT3 and ICAM4 (R2=0.76, r=0.87), and FLT3 and EDIL3 (R2=0.72, r=0.85). AECA levels specific for these four targets decreased in post-transplant sera (≤3 months) in nearly all cases (93%, 140 of 150 patients).

TABLE 3

Patient demographics for AECA ELISA categories

| ELISA Categories | Negative (N = 40) | Intermediate (N = 20) | Strongly Positive (N = 36) |
|---|---|---|---|
| ELISA Gene Values (mean; median) | | | |
| Endoglin | 1058; 992 | 9,375; 6,826 | 37,432; 26,101 |
| Flt3 | 1,311; 1,105 | 7,831; 6333 | 29,876; 19,104 |
| EDIL3 | 324; 0 | 5,880, 4,397 | 34,213; 23,290 |
| ICAM4 | 3,215; 3,272 | 17,053; 15,028 | 56,839; 32,896 |
| Recipient Age (mean ± SD) | 52 ± 16 | 49 ± 13 | 47 ± 15 |
| Race (non-white) | 40% | 40% | 50% |
| Male Gender | 25% | 50% | 44% |
| Previous transplantation | 40% | 50% | 39% |
| HLA Sensitization[1] | 90% | 90% | 97% |
| Mean % CPRA[2] (CDC-XM, FCXM) | 27, 37 | 27, 38 | 35, 44 |
| Original ABO or HLA barrier[3] | | | |
| ABOi | 10% | 15% | 18% |
| CDC-XM+ | 2% | 0% | 6% |
| FCXM+ | 15% | 15% | 19% |
| FCXM−, DSA+ | 48% | 55% | 50% |
| NO DSA | 35% | 30% | 25% |
| Donor (Mean Age ± SD) | 38 ± 13 | 43 ± 12 | 42 ± 16 |
| Live Donor (%) | 45% | 55% | 58% |
| HLA-A; B; DR; DQ mismatch (mean) | 4.7 | 4.1 | 5.2 |
| Plasmapheresis Treatments | | | |
| NO Pre- or Post-Treatments | 50% | 35% | 42% |
| Pre-transplant (mean, median) | 1.0, 0.0 | 1, 1 | 0.5, 0.0 |
| anti-CD25 induction | 17% | 20% | 15% |
| Thymoglobulin induction | 83% | 80% | 85% |
| Rituximab induction | 33% | 45% | 38% |

[1]HLA-specific antibody detected on Luminex ® bead immunoassays
[2]Calculated panel reactive antibody (CPRA) was determined for HLA-antibodies of sufficient strength to yield a positive CDC crossmatch (CDC-XM) or flow cytometric cross-match (FCXM)
[3]Original donor HLA-specific antibody (DSA) strength prior to desensitization treatment Example 5: AECA Activation of Endothelial Cell Cultures Primary endothelial cell cultures were established and stimulated with negative control serum, AECA positive sera, AECA eluates, TNFα, or a serum containing HLA antibodies. AECA eluates from five of the original ten Discovery Cohort recipients were used as stimulants. The eluates contained a concentration of AECAs compared to the original serum.

Cultured endothelial cells were stimulated for 24 hours, after which surface phenotype analysis was performed using flow cytometry to assess endothelial cell activation. We observed significant increases in the expression of HLA class I (p=0.04) and adhesion molecules: E selectin (p=0.02), and ICAM1 (p=0.005) following stimulation with the AECA eluates compared to negative control serum (data not shown) or the original AECA positive sera from which the eluates were derived (FIG. 4). The increase in platelet/endothelial cell adhesion molecule 1 (PECAM1) following AECA eluate stimulation was not statistically different from the negative controls (p=0.12). Stimulation of endothelial cell cultures using TNFα or serum containing HLA antibodies increased expression of all markers (HLA class I, PECAM1, E selectin, and ICAM1) compared to negative controls.

Figure 5:
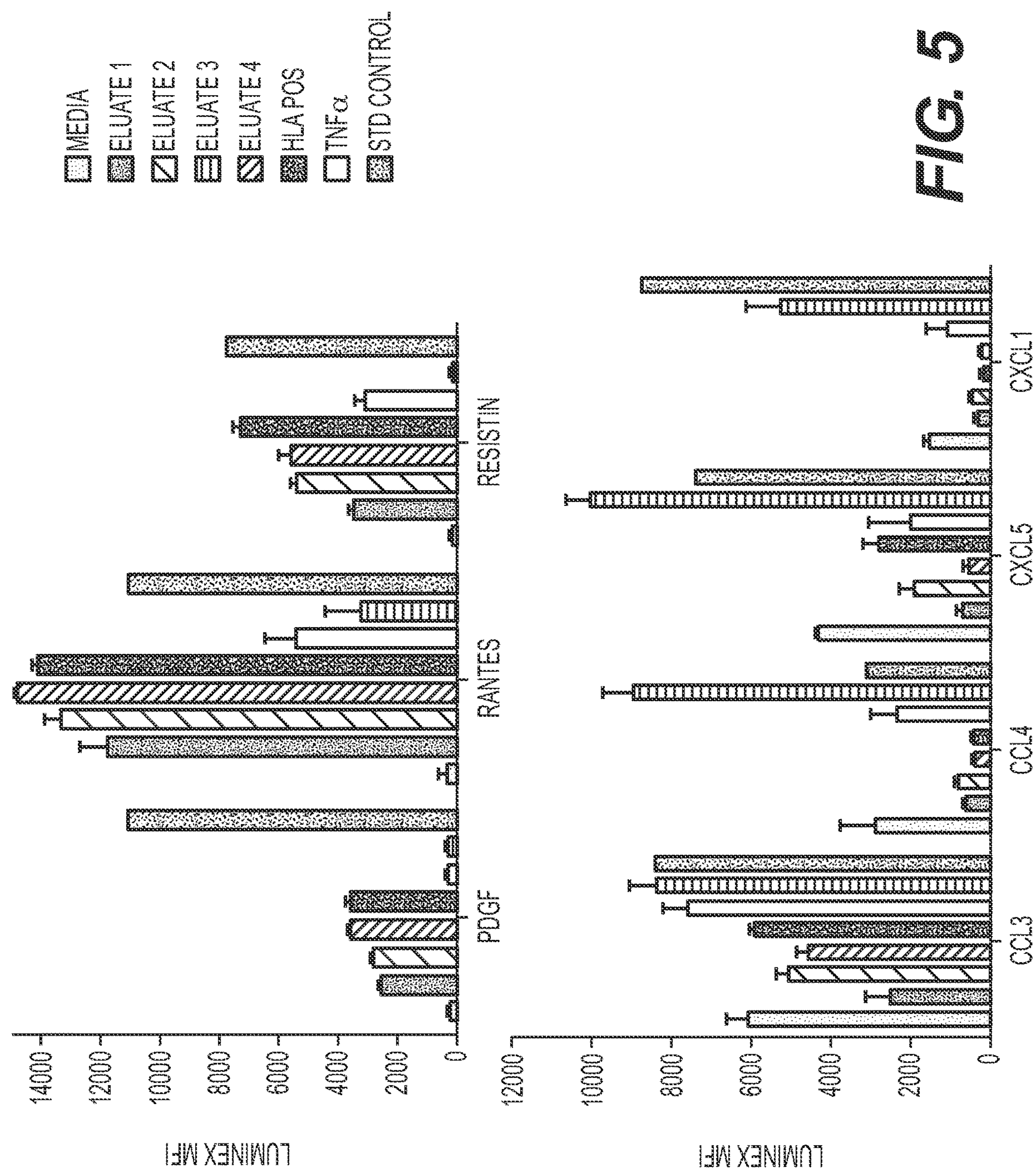

We assessed the production of inflammatory cytokines and chemokines after AECA eluate stimulation using a multiplexed immunoassay run on a Luminex® platform. Proteins and cytokines assayed for indications of endothelial cell activation are shown in Table 4. Primary endothelial cell cultures were stimulated with culture medium alone, negative control serum, AECA eluates, TNFα, or serum containing HLA antibodies specific for the ECP donor. After 72 hours, culture supernatants were harvested and tested in an Affymetrix Procarta® human immunoassay. Forty-four of the 54 analytes were negative in all supernatants tested. Interleukin (IL) 8, IL1 receptor antagonist (IL-1RA), and Serpin E1 were detected in all test cultures, including those without stimulation (culture medium alone) Inflammatory cytokines PDGF, RANTES (also known as CCL5), and RESISTIN were increased in cultures stimulated with the AECA eluates when compared to negative controls or cultures stimulated with TNFα or HLA antibodies (FIG. 5). In contrast, chemokines CCL3, CCL4, CXCL5, and CXCL appeared decreased in cultures stimulated with the AECA eluates compared to other stimulants.

TABLE 4

Proteins and Cytokines Indicative of Endothelial Cell Activation

| Protein Description | Gene Symbol | Gene ID No. |
|---|---|---|
| nerve growth factor (beta polypeptide) | NGF (beta-NGF) | 4803 |
| CD40 ligand | Cd40LG (CD40 ligand) | 959 |
| epidermal growth factor | EGF (EGF) | 1950 |
| chemokine (C—X—C motif) ligand 5 | CXCL5 (ENA-78) | 6374 |
| chemokine (C-C motif) ligand 11 | CCL11 (Eotaxin) | 6356 |
| fibroblast growth factor 2 (basic) | FGF2 (FGF basic) | 2247 |
| chemokine (C—X3—C motif) ligand 1 | CX3CL1 (Fractalkine) | 6376 |
| colony stimulating factor 3 receptor (granulocyte) | CSF3R (G-CSF) | 1441 |
| colony stimulating factor 2 receptor, beta, low-affinity (granulocyte-macrophage) | CSF2RB (GM-CSF) | 1439 |
| chemokine (C—X—C motif) ligand 1 (melanoma growth stimulating activity, alpha) | CXCL1 (GRO alpha) | 2919 |
| hepatocyte growth factor (hepapoietin A; scatter factor) | HGF (HGF) | 3082 |
| peroxisome proliferator-activated receptor gamma | PPARG (IFN alpha 2) | 5468 |
| interferon, alpha 1 | IFNA1 (IFN beta) | 3439 |
| interferon, alpha 1 | IFNA1 (IFN gamma) | 3439 |
| interleukin 1, alpha | IL1A (IL-1 alpha) | 3552 |
| interleukin 1, beta | IL1B (IL-1 beta) | 3553 |
| interleukin 1 receptor antagonist | IL1RN (IL-1RA) | 3557 |
| interleukin 2 | IL2 (IL-2) | 3558 |
| interleukin 4 | IL4 (IL-4) | 3565 |
| interleukin 5 | IL5 (IL-5) | 3567 |
| interleukin 6 | IL6 (IL-6) | 3569 |
| interleukin 7 | IL7 (IL-7) | 3574 |
| chemokine (C—X—C motif) ligand 8 | CXCL8 (IL-8) | 3576 |
| interleukin 9 | IL9 (IL-9) | 3578 |
| interleukin 10 | IL10 (IL-10) | 3586 |
| interleukin 12 | IL12B (IL-12) | 3593 |
| interleukin 12B | IL12B (IL-12 p70) | 3593 |
| interleukin 13 | IL13 (IL-13) | 3596 |
| interleukin 15 | IL15 (IL-15) | 3600 |
| interleukin 16 | IL16 (IL-16) | 3603 |
| interleukin 17A | IL17A (IL-17A) | 3605 |
| interleukin 17F | IL17F (IL-17F) | 112744 |
| interleukin 20 | IL20 (IL-20) | 50604 |
| chemokine (C—X—C motif) ligand 10 | CXCL10 (IP-10) | 3627 |
| chemokine (C—X—C motif) ligand 11 | CXCL11 (I-TAC) | 6373 |
| leptin receptor | LEPR (Leptin) | 3953 |
| chemokine (C-C motif) ligand 2 | CCL2 (MCP-1) | 6347 |
| chemokine (C-C motif) ligand 7 | CCCL7 (MCP-3) | 6354 |
| vascular endothelial growth factor A | VEGFA (M-CSF) | 7422 |
| chemokine (C—X—C motif) ligand 9 | CXCL9 (MIG) | 4283 |
| transportin 1 | TNPO1 (MIP-1 alpha) | 3842 |
| transportin 1 | TNPO1 (MIP-1 beta) | 3842 |
| chemokine (C-C motif) ligand 23 | CCL23 (MIP-3 alpha) | 6368 |
| serpin peptidase inhibitor, clade E (nexin, plasminogen activator inhibitor type 1), member 1 | SERPINE1 (PAI-1) | 5054 |
| platelet-derived growth factor beta polypeptide | PDGFB (PDFG-BB) | 5155 |
| chemokine (C-C motif) ligand 5 | CCL5 (RANTES) | 6352 |
| resistin | RETN (Resistin) | 56729 |
| serum amyloid A1 | SAA1 (SAA) | 6288 |
| transforming growth factor, alpha | TGFA (TFG alpha) | 7039 |
| transforming growth factor, beta 1 | TGFB1 (TGF beta 1*) | 7040 |
| tumor necrosis factor | TNF (TNF alpha) | 7124 |
| lymphotoxin alpha | LTA (TNF beta) | 4049 |
| tumor necrosis factor (ligand) superfamily, member 10 | TNFSF10 (TRAIL) | 8743 |
| vascular endothelial growth factor A | VEGFA (VEGF-A) | 7422 |

Example 6 Clinical Outcomes for Recipients Testing AECA Positive

We performed a preliminary analysis of the clinical outcomes for 40 recipients with the lowest reacting sera on the ELISAs, an intermediate group of 20 recipients that tested above the trimmed mean for antibodies specific for one to three target antigens, and 36 recipients who tested strongly positive for antibodies against all four targets: endoglin, EDIL3, ICAM4 and FLT3 (Table 2). Sera from the remaining recipients tested below the trimmed mean in ELISAs for all four target antigens. The demographics for these cohorts were similar for all pre-transplantation characteristics. Importantly, HLA-DSA strength at time of transplantation was similar between all three ELISA cohorts.

Twenty-eight percent of the ELISA positive group and 25% of the intermediate group experienced delayed graft function, requiring post-transplant dialysis, compared to 15% in the ELISA negative cohort (Table 5). The incidence of cellular rejection was not significantly different between the three ELISA groups, however, antibody mediated rejection was significantly higher in recipients that tested positive for AECAs (Intermediate: 15%, p=0.04 and strongly positive: 19%, p=0.007) compared to 4% in recipients that tested ELISA negative. Analysis of eighty-six biopsies from 36 recipients with the strongest reacting sera (68 indication and 18 protocol biopsies) revealed significantly more glomerulitis, peritubular capillaritis, C4d positivity, and transplant glomerulopathy than biopsies from the 40 ELISA negative recipients (36 indication and 34 protocol biopsies) (Table 5 and FIG. 6). The intermediate group (31 indication and 36 protocol biopsies) showed less glomerulitis, but more peritubular capillaritis, C4d positivity, and chronic vascular changes than the negative group. The incidence of HLA-DSA at time of biopsy was high, reflecting the high degree of HLA sensitization and the inclusion of incompatible transplants in these patient cohorts (Table 5). HLA-DSA was detected at the time of biopsy in 76% of biopsies from the ELISA positive recipients, 45% of biopsies from the intermediate positive recipients, and 47% of biopsies from ELISA negative recipients. Recipients that tested strongly positive for AECAs had a greater number of DSAs at time of biopsy and an increased incidence of antibodies to both HLA class I and class II antigens. We eliminated from a subsequent analysis, biopsies with high level HLA-DSA sufficient to yield a positive flow cytometric or cytotoxicity lymphocyte crossmatch test to examine the impact of low level HLA-DSA and AECAs. Among remaining biopsies with no or low level HLA-DSA, detected only by bead assays, more microvascular injury was still observed in the strongly positive versus AECA negative recipients (Table 5 and FIG. 6). Histopathology scores for microvascular injury were not significantly increased in biopsies from recipients with intermediate levels of AECAs with no or low HLA-DSA.

Serum creatinine levels in the immediate post-transplant period (7 days) were significantly higher in the ELISA positive group (p=0.002), corresponding to the high incidence of delayed graft function. The mean serum creatinine at 1 month was higher in the ELISA positive group (1.80±1.07) compared to the ELISA negative group (1.38±1.02) but the difference was not significant (p=0.09). Mean serum creatinine levels at 3 months, 1 year and ≥1.5 year were also higher than the ELISA positive cohort but not significantly different. Estimated glomerular filtration rate was not significantly different at any time-point post-transplantation (data not shown).

TABLE 5

Correlation Between AECA ELISAs and Clincal Outcome

| ELISA Categories: | Negative N = 40 | Intermediate N = 20 | p value | Strongly Positive N = 36 | p value |
|---|---|---|---|---|---|
| Graft Losses[1] (No.) | 0 | 0 | 1.0 | 1 | 0.47 |
| Delayed graft function[2] (%) | 15% | 25% | 0.48 | 28% | 0.26 |
| Acute rejection3 <1 yr (% biopsies) | 25% | 32% | 0.76 | 37% | 0.33 |
| CMR (N) | 15, 21% | 13, 19% | 0.83 | 16, 19% | 0.69 |
| AMR (N) | 3, 4% | 10, 15% | 0.04 | 16, 19% | 0.007 |
| Time $1^{st}$ rejection (Days: Mean, Median) | 131, 102 | 76, 17 | 0.63 | 67, 19 | 0.18 |
| Donor-specific HLA antibody (HLA-DSA) | | | | | |
| % All biopsies | 44% | 34% | 0.16 | 75% | 0.0001 |
| % Luminex ® only biopsies | 25% | 24% | 0.39 | 38% | 0.008 |
| Number DSA All biopsies (mean) | 0.8 ± 1.1 | 1.3 ± 1.5 | 0.04 | 2.5 ±1.9 | $4.7 \times 10^{-7}$ |
| Class I (N, % of biopsies) | 11, 14% | 5, 7% | 0.18 | 14, 17% | 1.0 |
| Class II (N, % of biopsies) | 12, 14% | 14, 21% | 0.66 | 24, 28% | 0.13 |
| Class I & II (N, % of biopsies) | 8, 11% | 5, 7% | 0.56 | 26, 31% | 0.006 |
| Glomerulitis (g 0-3) mean | | | | | |
| All biopsies | 0.4 ± 0.5[4] | 0.2 ± 0.4[5] | 0.0004 | 0.7 ± 0.9[6] | 0.004 |
| No/Low HLA-DSA | 0.4 ± 0.5 | 0.1 ± 0.3 | 0.0006 | 0.5 ± 0.6 | 0.47 |
| Inflammation (i 0-3) mean | | | | | |
| All biopsies | 0.8 ± 0.9 | 0.8 ± 0.9 | 0.79 | 0.7 ± 0.9 | 0.79 |
| No/Low HLA-DSA | 0.7 ± 0.9 | 0.5 ± 0.6 | 0.14 | 0.6 ± 0.7 | 0.53 |
| Tubulitis (t 0-3) mean | | | | | |
| All biopsies | 0.7 ± 0.8 | 0.8 ± 0.9 | 0.78 | 0.8 ± 0.8 | 0.41 |
| No/Low HLA-DSA | 0.6 ± 0.8 | 0.5 ± 0.6 | 0.43 | 0.8 ± 0.8 | 0.11 |
| Vasculitis (v 0-3) mean | | | | | |
| All biopsies | 0.1 ± 0.2 | 0.2 ± 0.5 | 0.18 | 0.3 ± 0.6 | 0.004 |
| No/Low HLA-DSA | 0.1 ± 0.2 | 0.0 ± 0.2 | 0.82 | 0.1 ± 0.4 | 0.23 |
| Peritubular capillaritis (ptc 0-3) mean | | | | | |
| All biopsies | 0.6 ± 1.1 | 1.1 ± 1.3 | 0.04 | 1.4 ± 1.4 | $5.1 \times 10^{-5}$ |
| No/Low HLA-DSA | 0.4 ± 0.9 | 0.6 ± 1.1 | 0.33 | 1.1 ± 1.3 | 0.002 |
| C4d (0-3) mean | | | | | |
| All biopsies | 0.1 ± 0.4 | 0.6 ± 1.1 | 0.004 | 0.7 ± 1.2 | $6.8 \times 10^{-5}$ |
| No/Low HLA-DSA | 0.0 ± 0.0 | 0.0 ± 0.2 | 0.22 | 0.3 ± 0.9 | 0.02 |
| Transplant glomerulopathy (cg 0-3) mean | | | | | |
| All biopsies | 0.1 ± 0.3 | 0.0 ± 0.3 | 0.85 | 0.3 ± 0.7 | 0.01 |
| No/Low HLA-DSA | 0.1 ± 0.3 | 0.0 ± 0.0 | 0.35 | 0.3 ± 0.7 | 0.05 |

TABLE 5-continued

Correlation Between AECA ELISAs and Clincal Outcome

| ELISA Categories: | Negative N = 40 | Intermediate N = 20 | p value | Strongly Positive N = 36 | p value |
|---|---|---|---|---|---|
| IFTA (ci 0-3 & ct 0-3) mean | | | | | |
| All biopsies | 1.4 ± 1.4 | 1.9 ± 1.8 | 0.12 | 1.5 ± 1.5 | 0.43 |
| No/Low HLA-DSA | 1.0 ± 1.3 | 1.4 ± 1.5 | 0.07 | 1.7 ± 1.5 | 0.009 |
| Cv 0-3, mean | | | | | |
| All biopsies | 0.7 ± 0.8 | 1.1 ± 1.1 | 0.02 | 0.9 ± 1.0 | 0.11 |
| No/Low HLA-DSA | 0.6 ± 0.8 | 0.9 ± 1.0 | 0.08 | 0.9 ± 0.9 | 0.08 |
| Serum Creatinine (mean + SD) | | | | | |
| 7 Day | 2.39 ± 2.25 | | | 4.69 ± 4.27 | 0.002 |
| 1 month | 1.38 ± 1.02 | 1.77 ± 0.97 | | 1.80 ± 1.07 | 0.09 |
| 3 month | 1.33 ± 0.64 | 1.90 ± 1.62 | | 1.80 ± 1.07 | 0.09 |
| 12 month | 1.40 ± 0.56 | 1.73 ± 1.47 | | 1.61 ± 1.47 | 0.48 |
| Last available value | 1.73 ± 1.47 | 2.05 ± 2.10 | | 2.59 ± 2.88 | 0.11 |
| (months post-transplant: mean + SD) | (18.8 ± 13.4) | (19 ± 2.1) | | (24.5 ± 14.9) | 0.09 |

[1]Graft loss due to accelerated vascular rejection

[2]Post-transplant dialysis

[3]Diagnosed antibody and cellular mediated rejection using updated Banff 1997-2007 criteria.

[4]Seventy total biopsies (34 protocol) and 56 biopsies (28 protocol) with No or Low HLA-DSA (detected by Luminex ® only).

[5]Sixty-seven total biopsies (36 protocol) and 46 biopsies (30 protocol) with No or Low HLA-DSA (detected by Luminex ® only).

[6]Eighty-six total biopsies (18 protocol) and 55 biopsies (16 protocol) with No or Low HLA-DSA (detected by Luminex ® only).

Example 7: Patients

Clinical data and stored sera from 160 renal transplant recipients, transplanted between 2009-2011, were studied retrospectively following IRB approval. Sera from a discovery group of ten recipients, who tested positive in endothelial cell crossmatch tests and experienced allograft rejection in the first 3 months post-transplant, in the absence of donor HLA-specific antibody, were tested on a protein array platform. ELISA tests were performed on 150 sequential renal transplant recipients for whom there were adequate pre- and post-transplant (≤3 months) sera. Patient demographics are provided in Table 1.

Example 8 Immunosuppressive Treatments of Patients

Maintenance immunosuppression included mycophenolate mofetil (2 gm/day), tacrolimus (serum level of 8-10 ng/ml), and prednisone (30 mg/day). Prednisone was reduced to 20 mg/day when tacrolimus reached therapeutic range (8-12 ng/dL) and tapered thereafter to 5 or 10 mg/day. Intraoperative induction therapy was either anti-IL2 receptor antibody (anti-CD25, daclizumab 2 mg/kg) or Thymoglobulin (1.5 mg/kg per day for 5 days). HLA and ABO incompatible pairs were included in this study. Desensitization included alternate day plasmapheresis immediately followed by low dose (100 mg/kg) intravenous immunoglobulin (IVIg) (Cytogam-CSL Behring, King of Prussia, Pa.). Mycophenolate mofetil (2 g/day) and tacrolimus (serum level of 8-10 ng/mL) were initiated with the start of plasmapheresis treatments. The number of treatments was dependent on ABO or donor HLA-specific antibody (HLA-DSA) titer. Biopsy confirmed acute cellular rejection was treated with pulse solumedrol at cumulative doses of 30-50 mg/kg in 3-6 doses and increased baseline target levels for tacrolimus and/or mycophenolate mofetil. Biopsy confirmed acute antibody mediated rejection (AMR) was treated with plasmapheresis and/or rituximab and/or IVIg and pulse solumedrol.

Example 9 HLA Antibody Detection and Cross-match Tests

HLA-specific antibodies were evaluated prior to transplantation and at time of biopsy using solid-phase immunoassays (Lifecodes class I and II ID panels, Immucor-Lifecodes, Stamford, Conn. and Single Antigen Beads, One Lambda, Canoga Park, Calif.) performed on a Luminex® platform. Crossmatch tests with donor T and B cells were performed using standard cytotoxicity and/or flow cytometry (FCXM) protocols. Calculated panel reactive antibody was determined for antibodies sufficient to yield a positive cytotoxicity or FCXM using virtual crossmatch methods and the online UNOS CPRA calculator 20. AECAs were detected using a FCXM performed using angiopoietin receptor (Tie-2) positive, peripheral blood ECPs (XM-ONE®

Example 10 Derivation of Non-HLA Anti-Endothelial Cell Antibody Eluates

AECA eluates were derived from absorbing antibody from endothelial cell crossmatch positive sera onto Tie2+ ECPs isolated from surrogate donors to whom there was no HLA-DSA. The serum to cell ratio, incubation, and wash steps were consistent with the endothelial cell crossmatch procedure. Antibody was acid eluted in 1/10 of the original serum volume as previously described and dialyzed 18 hours against phosphate buffered saline. AECA eluates were retested in endothelial cell crossmatch tests to ensure antibody integrity and specificity. Absorber AB, Stockholm, Sweden) acquired on a BD FACSAria™ using FACSDiva (version 6.1.1, BD Biosciences, Franklin Lakes, N.J.).

Example 11 Protein Microarray Analyses

ProtoArray® Human Protein Microarrays v5.0 (Life Technologies, Foster City, Calif.) were used to profile antibodies present in 14 AECA eluates from ten endothelial cell crossmatch positive recipients. For two recipients, analysis was performed on AECA eluates derived from sera obtained prior to and following desensitization treatments. The protein arrays contained approximately 9500 recombinant human proteins expressed as N-terminal GST fusion proteins and spotted on the nitrocellulose-coated glass slide. Established protocols (www.invitrogen.com) were followed 23, 24 for sample preparation, blocking, probing, drying by centrifugation, scanning, and data acquisition. Slides were scanned using an Axon GenePix 4000B Scanner (Molecular Devices. Sunnyvale, Calif.) and GenePix pro 6.0 software (Molecular devices, Sunnyvale, Calif.). We used data analysis software ProtoArray® Prospector 5.2 to analyze any bound IgG antibody detected by the secondary Alexa Fluor® 647-conjugated antibody. Binding of the secondary antibody on the microarray was then quantified by measuring the fluorescence intensity of each feature on the slide. Data generation and normalization involved calculating appropriate fluorescent signal values taking into account corrections for background and negative control features printed on the microarray. Z-Factors for all the corrected intensities of the human protein features were calculated and the features that had signal intensities greater than the cut-off value of 2000 was considered as abundant signal. Pathway analysis was performed using Ingenuity Pathway analysis (Ingenuity® Systems, www.ingenuity.com) and GO-Elite Pathway Analysis Tool (www.genmapp.org/go_elite/go_elite.html).

Example 12 Endothelial Cell Antigen Specific ELISAs

EC specific antigen targets identified by protein arrays were validated using the MSD ELISA platform (Meso Scale Discovery, Gaithersburg, Md.). Recombinant proteins/antigens obtained from Abcam (Cambridge, Mass.) included: EDIL3 (Cat No. ab94549), FLT3 (Cat No. 83996), Endoglin (Cat No. ab95043), and recombinant ICAM4 (Cat No. H00003386-P) was purchased from Abnova (Walnut, Calif.). To increase detection specificity and sensitivity, each antigen was biotin conjugated and incubated with diluted serum before coating the antigen-antibody complex onto the avidin coated ELISA plate. Biotin labeling of each antigen (5 μg) was performed using EZ-Link Sulfo-NHS-LC_Biotin (Cat No. PI21335, Rockford, Ill.), EZ BIOTIN QUANTIFICATION KIT (Cat No. PI28005, Rockford, Ill.), and Zeba* Spin Desalting Columns (7K MWCO, 5 mL, Cat No. PI89892, Rockford, Ill.) following the manufacturer's protocol. The serum was diluted 1:75 with 2% Blocker A (Cat. No. R93AA-1, Meso Scale Discovery, Gaithersburg, Md.) in TPBS, after titration studies showed this to be the optimal dilution. Equal parts of diluted serum (50 μL) and biotin-labeled antigen (5 ng) or 2% Blocker A in TPBS were added to a Streptavidin Gold Plate (Cat. No. L15SA-1, Meso Scale Discovery, Gaithersburg, Md.) and incubated for 90 min at room temperature with shaking (300 rpm). The plate was blocked with 5% Blocker A (150 μL) for 90 minutes at room temperature with shaking, washed once with 300 uL TPBS, and 100 μL diluted Goat Anti-Human SULFO-TAG (1:1000) detection antibody was added and incubated in the dark for 60 minutes at room temperature with shaking. Following three washes with 300 μl TPBS, 150 μL reading buffer was added to each well and the plate was immediately read with a SECTOR® Imager 2400 (Meso Scale Discovery, Gaithersburg, Md.). Reactivity above the trimmed mean was considered positive and changes between pre- and post-transplant antibody levels were determined by increases or decreases that exceeded a 95% confidence interval for each ELISA.

Example 13 Endothelial Cell Culture

Primary endothelial cell cultures were established using Tie2+ ECPs isolated from donors that yielded a positive endothelial cell crossmatch test with sera from the Discovery Cohort as previously described 25. In brief, ECPs were isolated using Tie2 magnetic beads (XM-ONE® Absorber AB, Stockholm, Sweden), plated at a 1000 cells/mm2 density in fibronectin (1 ug/well) coated wells, and cultured for 2-3 weeks in supportive media (EGM-2 Bullet Kit, Lonza, Walkersville, Md.) to allow for maturation. EC lines (CRL-2606TM, ATCC and HuVEC, gift of Dr. Mark K Halushka) were cultured as above; cultures were passed when 70-80% confluent and analyzed within the first 5 passages.

Example 14 Analysis Following Endothelial Cell Culture Stimulation

Primary endothelial cell cultures were washed twice with wash buffer (lx PBS with 5% heat inactivated, fetal calf serum). Cells were stimulated using 100 μL of negative control AB serum, endothelial cell crossmatch positive sera, AECA eluates, TNFα (10 ng/well, Abcam, Cambridge, Mass.), or a serum containing antibodies specific for HLA antigens of the ECP donor. Cells were incubated for 1 hour after which 1 ml of supportive media was added to each well. Cell surface phenotype analysis was performed 24 hours post stimulation. Cells were removed with 0.25% trypsin, washed, and stained according to standard protocols. Monoclonal antibodies included peridinin chlorophyll protein complex conjugated CD54 (clone HA58), phycoerythrin conjugated CD62E (clone 68-5H11), fluorescein isothiocyanate conjugated HLA class I (clone G46-2.6) and CD3 (clone SK7), Alexa Fluor 647 congugated CD31 (cloneWM59) (BD Biosciences, Franklin Lakes, N.J.). Rabbit anti-human polyclonal antibodies included CD105 (Endoglin, ab21224), CD242 (ICAM4, ab112554), EDIL3 (ab74775), and CD135 (FLT3, ab37847) (Abcam, Cambridge, Mass.). Allophycocyanin conjugated goat anti-rabbit IgG was purchased from R&D Systems (Minneapolis, Minn.). Cells were acquired (2000 gated events) and analyzed using a BD FACSAria™ and FACSDiva (version 6.1.1, BD Biosciences) and/or De Novo Software™ (Los Angeles, Calif.). Following 72 hours of stimulation, culture supernatants were tested using the Procarta® human 54 analyte immunoassay (Affymetrix Inc., Santa Clara, Calif.) according to manufacturer's protocol and acquired on a Luminex® xMAP® multiplex platform. Each assay included a positive control standard for each target protein. Histopathogy All biopsies performed during the first year post-transplantation were included in the analysis. Biopsies were performed at time of graft dysfunction and for HLA incompatible recipients, according to protocol at 1, 3, 6, and 12 months post-transplantation. Recipients may be excluded from protocol biopsies due to anti-coagulation therapy or if the intra-abdominal transplant cannot be safely biopsied. Biopsies were scored using updated Banff '97 criteria 26-29. Criteria for diagnosis of antibody mediated rejection included detection of C4d by indirect immunofluorescence. C4d staining was considered positive if present in ≥50% of the peritubular capillaries with intensity≥1+(C4d2-3). Additional staining of biopsy tissue was performed using rabbit anti-human polyclonal antibodies reactive with CD105

(RB9291P1, Thermo Fisher Scientific Inc., Waltham, Mass.), CD242 (ICAM4, ab112554), EDIL3 (ab74775), and CD135 (FLT3, ab37847) (Abcam, Cambridge, Mass.). Detection was performed using a horseradish peroxidase polymer conjugated secondary antibody (SuperPicture™ Polymer Detection Kit, Life Technologies, Grand Island, N.Y.).

Example 15 Statistical Methods

Protein array data was analyzed by Prospector Analyzer (Life Technologies, Foster City, Calif.) using robust linear model normalization 30. A minimum relative fluorescent unit (RFU) >500 and a Z-factor of 0.4 was required for positive detection. Summary statistics including mean, trimmed mean, median, confidence norm distribution, correlation coefficient, coefficient of difference, and standard deviation were calculated using Microsoft Excel. Statistical significance was determined using Chi squared and Student's t tests (two tailed) and p values of <0.05 were considered significant.

We claim:

1. A method of treating an individual who has received an organ transplant, comprising:

(1) increasing the administration of a therapeutically effective amount of one or more immunosuppressive therapeutics if the individual's antibody expression profile indicates that the individual has an increased risk of developing allograft rejection (AR);

(2) maintaining the administration of a therapeutically effective amount of one or more immunosuppressive therapeutics if the individual's antibody expression profile indicates that the individual does not have an increased or decreased risk of developing AR; or (3) decreasing the administration of a therapeutically effective amount of one or more immunosuppressive therapeutics if the individual's antibody expression profile indicates that the individual has a decreased risk of developing AR;

wherein the antibody expression profile comprises the level of at least four antibodies from a biological sample from the individual that form an affinity interaction with at least a portion or peptide fragment of at least four proteins selected from Table 2; and wherein a similarity of the level of the at least four antibodies to the positive reference standard indicates increased risk of developing AR and a similarity of the measured level of the at least four antibodies to the negative reference standard indicates decreased risk of developing AR.

2. The method of claim 1, wherein the biological sample is selected from the group consisting of whole blood, blood, serum, plasma, urine, mucus, saliva, cerebrospinal fluid, tissues, biopsies and combinations thereof.

3. The method of claim 2, wherein the at least four antibodies are anti-endothelial cell antibodies.

4. The method of claim 3, wherein the anti-endothelial cell antibodies form an affinity interaction with endoglin, Fms-like tyrosine kinase-3 (FLT3) ligand, EGF-like repeats and discoidin I-like domains 3 (EDIL3), and intercellular adhesion molecule 4 (ICAM4).

5. The method of claim 1, further comprising isolating the at least four antibodies by incubating the biological sample with an antibody capture element.

6. The method of claim 5, wherein the antibody capture element comprises an antibody specific antigen, a capture bead, and capture solid support.

7. The method of claim 6, wherein the antibody capture element comprises an antibody specific antigen.

8. The method of claim 7, wherein the antibody specific antigen is selected from the group consisting of: a full length protein, protein fragment, peptide, polypeptide, recombinant peptide, recombinant protein, and a polypeptide fragment.

9. The method of claim 8, wherein the antibody specific antigen comprises at least a portion or peptide fragment of at least four proteins selected from Table 2.

10. The method of claim 9, wherein the at least four proteins are endoglin, Fms-like tyrosine kinase-3 (FLT3) ligand, EGF-like repeats and discoidin I-like domains 3 (EDIL3) and intercellular adhesion molecule 4 (ICAM4).

11. The method of claim 7, wherein the antibody specific antigen is labelled with an isolation tag selected from the group consisting of biotin, a GST tag, an amide group, and a streptavidin tag.

12. The method of claim 11, wherein the isolation tag is a biotin.

13. The method of claim 5, wherein the antibody capture element is isolated with a secondary capture element.

14. The method of claim 13, wherein the secondary capture element is immobilized on a solid support comprising a bead or a plate.

15. The method of claim 13, wherein the secondary capture element comprises streptavidin.

16. The method of claim 1, further comprising measuring the level of the at least four antibodies by a detection element.

17. The method of claim 16, wherein the detection element comprises a labelled secondary antibody.

18. The method of claim 1, wherein the antibody expression profile further comprises the level of a donor specific HLA antibody.

19. The method of claim 18, wherein the level of the donor specific HLA antibody is detected by a cell based assay or a solid-phase immunoassay.

20. The method of claim 19, wherein the solid-phase immunoassay comprises an ELISA, and wherein the cell based assay comprises a cross-match assay.

21. The method of claim 1, further comprising administering pulse solumedrol and increased baseline target levels of a therapeutically effective amount of one or more immunosuppressive therapeutics if the individual has an increased risk of developing AR.

22. The method of claim 21, wherein the pulse solumedrol is administered at cumulative doses of about 30 to about 50 mg/kg in 3-6 doses.

23. The method of claim 1, wherein the one or more immunosuppressive therapeutics are selected from: steroids, antibodies, calcineurin inhibitors, antiproliferatives, mammalian target of rapamycin (mTOR) inhibitors, and therapeutic plasmapheresis.

24. The method of claim 23, wherein the steroids comprise prednisone, prednisolone, and methyl-prednisolone.

25. The method of claim 23, wherein the antibodies comprise muromonab-CD3, antithymocyte immune globulin, daclizumab, basiliximab, Rituximab, cytomegalovirus-immune globulin, and immune globulin.

26. The method of claim 23, wherein the calcineurin inhibitors comprise cyclosporine, and tacrolimus.

27. The method of claim 23, wherein the antiproliferatives comprise mycophenolate mofetil, and azathioprine.

28. The method of claim 23, wherein the mTOR inhibitors comprise rapamycin, and everolimus.

29. The method of claim 18, wherein the presence of the donor specific HLA antibody indicates an increased risk for developing an AR.

* * * * *